United States Patent
Kuduk et al.

(10) Patent No.: US 8,293,744 B2
(45) Date of Patent: Oct. 23, 2012

(54) HETEROCYCLIC FUSED CINNOLINE M1 RECEPTOR POSITIVE ALLOSTERIC MODULATORS

(75) Inventors: Scott D. Kuduk, Harleysville, PA (US); Douglas C. Beshore, Lower Gwynedd, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/264,267

(22) PCT Filed: Apr. 13, 2010

(86) PCT No.: PCT/US2010/030814
§ 371 (c)(1),
(2), (4) Date: Oct. 13, 2011

(87) PCT Pub. No.: WO2010/123716
PCT Pub. Date: Oct. 28, 2010

(65) Prior Publication Data
US 2012/0040978 A1  Feb. 16, 2012

Related U.S. Application Data

(60) Provisional application No. 61/170,744, filed on Apr. 20, 2009.

(51) Int. Cl.
*A61K 31/50* (2006.01)
*C07D 237/36* (2006.01)

(52) U.S. Cl. ............... 514/252.06; 514/248; 514/252.01; 514/252.04; 514/252.05; 544/234

(58) Field of Classification Search .................. 544/234; 514/252.04, 252.05, 252.06, 252.01, 248
See application file for complete search history.

(56) References Cited

FOREIGN PATENT DOCUMENTS

| WO | WO2004073639 | 9/2004 |
| WO | WO2007067489 | 6/2007 |
| WO | WO2007143523 | 12/2007 |
| WO | WO2008068424 | 6/2008 |

OTHER PUBLICATIONS

R. M. Eglen et al., "Therapeutic Opportunities from Muscarinic Receptor Research", 2001, pp. 409-414, vol. 22, No. 8, Trends in Pharmacological Sciences.
A. Fisher, Therapeutic Strategies in Alzheimer's Disease: M1 Muscarinic Agonists, 2000, pp. 101-112, vol. 84, Jpn. J. Pharmacol.
T. A. Spalding et al., "Discovery of an Ectopic Activation Site on the M1 Muscarinic Receptor", 2002, pp. 1297-1302, Molecular Pharmacology.
S. Lazareno et al., "Analogs of WIN 62.577 Define a Second Allosteric Site on Muscarinic Receptors", 2002, pp. 1492-1505, vol. 62, Molecular Pharmacology.
S. Lazareno et al., "Allosteric Interactions of Staurosporine and Other Indolocarbazoles with N-[methyl-3-H] Scopolamine and Acetylcholine at Muscarinic Receptor Subtypes: Identification of a Second Allosteric Site",2000, pp. 194-207, vol. 58, Molecular Pharmacology.
M. P. Caulfield, "Muscarinic Receptors—Characterization, Coupling and Function", 1993, pp. 319-379, vol. 58, Pharma. Ther.
N. J. M. Birdsall et al., "Multiple Allosteric Sites on Muscarinic Receptors", 2001, pp. 2517-2524, vol. 68, Life Sciences.
A. Christopoulos et al., "Allosteric Binding Sites on Cell-Surface Receptors: Novel Targets for Drug Discovery", 2002, pp. 198-210, Natural Reviews, Drug Discovery.
H. Brauner-Osborne et al., "Pharmacology of Muscarinic Acetylcholine Receptor Subtypes (m1-m5): High Throughput Assays in Mammalian Cells". 1996, vol. 295, pp. 93-102, E. Journal of Pharmacology.
J. Peng et al., "The Predicted 3D Structures of the Human M1Muscarinic Acetylcholine Receptor with Agonist or Antagonist Bound", ChemMedChem, 2006, vol. 1, pp. 878-890, Wiley-VCH Verlag GmBH &Co.

*Primary Examiner* — Paul V. Ward
(74) *Attorney, Agent, or Firm* — Sylvia A. Ayler; Gerard M. Devlin

(57) ABSTRACT

The present invention is directed to heterocyclic fused cinnoline compounds of formula (I) which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

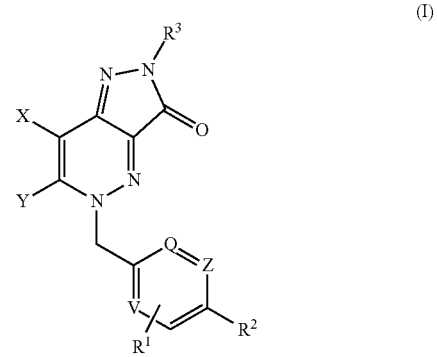

19 Claims, No Drawings

HETEROCYCLIC FUSED CINNOLINE M1 RECEPTOR POSITIVE ALLOSTERIC MODULATORS

CROSS REFERENCE TO RELATED APPLICATIONS

This application is the National Stage of International Application No. PCT/US2010/030814 filed on Apr. 13, 2010, which claims the benefit under 35 U.S.C. 119(e) of U.S. Provisional Application No. 61/170,744, filed Apr. 20, 2009.

FIELD OF THE INVENTION

The invention is directed to a class of heterocyclic fused cinnoline compounds, their salts, pharmaceutical compositions comprising them and their use in therapy of the human body. In particular, the invention is directed to a class of heterocyclic fused cinnoline compounds which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences*, 2001, 22:8, 409-414. In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacal*, 2000, 84:101-112.

However, M1 ligands which have been developed and studied for Alzheimer's Disease have produced side effects common to other muscarinic receptor ligands, such as sweating, nausea and diarrhea. See Spalding et al, *Mol Pharmacol*, 2002, 61:6, 1297-1302.

The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505; S. Lazareno et al, *Mol Pharmacol*, 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is directed to novel heterocyclic fused cinnoline compounds of generic formula (I)

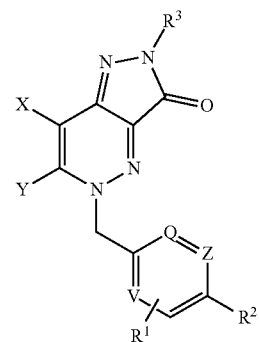

or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to heterocyclic fused cinnoline compounds of general formula (I)

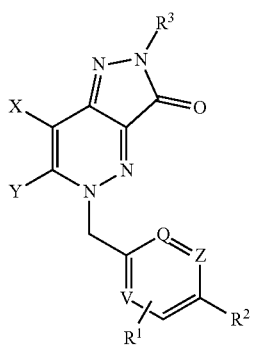

and pharmaceutically acceptable salts thereof, wherein
Q, V and Z are each selected from the group consisting of
1) —CH, and
2) N;
X and Y are linked together to form a fused ring moiety selected from the group consisting of

1)

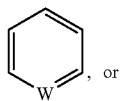, or (2)

;

W is selected from the group consisting of
1) —CH, and
2) —N;
$R^1$ is optionally present at one or more of the ring carbon atoms, and is selected from the group consisting of
(1) —$C_{1-6}$ alkyl,
(2) —O—$C_{1-6}$ alkyl, or
(3) halogen;
$R^2$ is selected from the group consisting of
(1) aryl,
(2) a heteroaryl group which is an aromatic cyclic group, having from five to twelve ring atoms, said ring atoms selected from C, O, N or S, at least one of which is O, N or S,
(3) halogen,
wherein said aryl or heteroaryl is optionally substituted with one or more
(a) halogen,
(b) hydroxy,
(c) —O—$C_{1-6}$ alkyl,
(d) —$C_{1-6}$ alkyl,
(e) cyano,
(f) —$NR^A R^B$, wherein $R^A$ and $R^B$ are selected from the group consisting of
(i) hydrogen, or
(ii) —$C_{1-6}$ alkyl, or $R^A$ and $R^B$ are linked together with the nitrogen to which they are both attached to form a 2-6 membered carbocyclic ring, wherein one or two of the ring carbon atoms is replaced by a nitrogen, oxygen or sulfur, and the carbocyclic is optionally substituted with one or more $C_{1-6}$ alkyl,
(g) —C(=O)—$R^C$, wherein $R^C$ is selected from the group consisting of
(i) hydrogen, or
(ii) —$C_{1-6}$ alkyl, or
(h) —$S(O)_n$—$R^C$;
$R^3$ is selected from the group consisting of
(1) aryl,
(2) a heteroaryl group, which is an aromatic cyclic group, having from five to twelve ring atoms, said ring atoms selected from C, O, N or S, at least one of which is O, N or S,
(3) —$C_{5-10}$ cycloalkyl, or
(4) a heterocyclic group, which is a nonaromatic cyclic group, having from five to twelve ring atoms, said ring atoms selected from C, O, N or S, at least one of which is O, N or S, wherein said aryl, heteroaryl cycloalkyl or heterocyclic group is optionally substituted with one or more
(a) halogen,
(b) hydroxy,
(c) —O—$C_{1-6}$ alkyl, or
(d) —$C_{1-6}$ alkyl;
n is 0, 1 or 2.

In particular embodiments of the compounds of formula (I), X and Y are linked together to form the fused ring moiety:

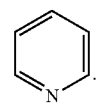

In other embodiments of the compounds of formula (I), X and Y are linked together to form the fused ring moiety:

In particular embodiments of the compounds of formula (I), V and Q are CH and Z is N.

In other embodiments of the compounds of formula (I), each of V, Q and Z are CR

In particular embodiments of the compounds of formula (I), $R^1$ is not present.

In particular embodiments of the compounds of formula (I), $R^2$ is optionally substituted heteroaryl. Exemplary $R^2$ heteroaryl groups include groups having five or six ring atoms, where one or two of the ring atoms is nitrogen and the others are all carbon (e.g., pyrazole or pyridine). Additional heteroaryl groups are groups having five or six ring atoms, having one nitrogen and one sulfur ring atoms, and the others are all carbon (e.g., thiazole).

In other embodiments, $R^2$ is optionally substituted aryl (for example, phenyl)

In still other embodiments, $R^2$ is halogen (suitably fluoro or chloro).

In particular embodiments of the compounds of formula (I), $R^3$ is optionally substituted Aryl (suitably, phenyl). Typically, the R3 phenyl group is substituted with one or more $C_{1-6}$ alkyl (e.g, methyl or ethyl), and/or with one or more halogen (suitably, fluoro or chloro).

In other embodiments, $R^3$ is heteroaryl. Exemplary $R^3$ heteroaryl groups include groups having five or six ring atoms, where one or two of the ring atoms is nitrogen and the others are all carbon (e.g., pyrazole or pyridine).

In other embodiments, $R^3$ is cycloalkyl (suitably, cyclopentyl or cyclohexyl). Typically, the $R^3$ heterocyclic group is unsubstituted or substituted with hydroxy. For example, $R^3$ may be

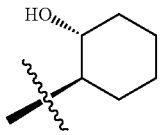

In other embodiments, $R^3$ is heterocyclic (suitably, tetrahydropyran). Typically, the $R^3$ heterocyclic group is unsubstituted or substituted with hydroxy. For example, $R^3$ may be:

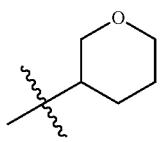

In one embodiment, the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I) with one or more pharmaceutically acceptable carriers.

Within the genus of compounds of formula (I), there is a sub-genus of compounds of formula (II):

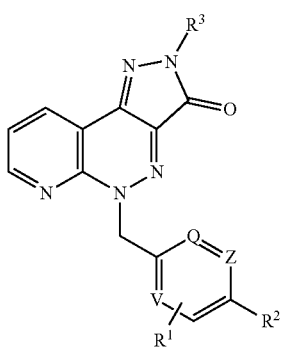

(II)

and pharmaceutically acceptable salts thereof, wherein V, Q, Z, $R^1$, $R^2$ and $R^3$ are as described above.

In particular embodiments of the compounds of formula (II), V and Q are CH and Z is N.

In other embodiments of the compounds of formula (II), each of V, Q and Z are CH.

In particular embodiments of the compounds of formula (II), $R^1$ is not present.

In particular embodiments of the compounds of formula (II), $R^2$ is optionally substituted heteroaryl. Exemplary $R^2$ heteroaryl groups include groups having five or six ring atoms, where one or two of the ring atoms is nitrogen and the others are all carbon (e.g., pyrazole or pyridine). Additional heteroaryl groups are groups having five or six ring atoms, having one nitrogen and one sulfur ring atoms, and the others are all carbon (e.g., thiazole).

In other embodiments, $R^2$ is optionally substituted aryl (for example, phenyl)

In still other embodiments, $R^2$ is halogen (suitably fluoro or chloro).

In particular embodiments of the compounds of formula (I), $R^3$ is optionally substituted Aryl (suitably, phenyl). Typically, the $R^3$ phenyl group is substituted with one or more $C_{1-6}$ alkyl, and/or with one or more halogen (suitably, fluoro or chloro), In other embodiments, $R^3$ is heteroaryl. Exemplary $R^3$ heteroaryl groups include groups having five or six ring atoms, where one or two of the ring atoms is nitrogen and the others are all carbon (e.g., pyrazole or pyridine).

In other embodiments, $R^3$ is cycloalkyl (suitably, cyclopentyl or cyclohexyl). Typically, the $R^3$ heterocyclic group is unsubstituted or substituted with hydroxy. For example, R3 may be

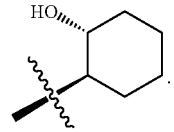

In other embodiments, $R^3$ is heterocyclic (suitably, tetrahydropyran). Typically, the $R^3$ heterocyclic group is unsubstituted or substituted with hydroxy. For example, $R^3$ may be:

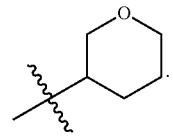

In one embodiment, the compounds of formula (II) are compounds of formula (IIA)

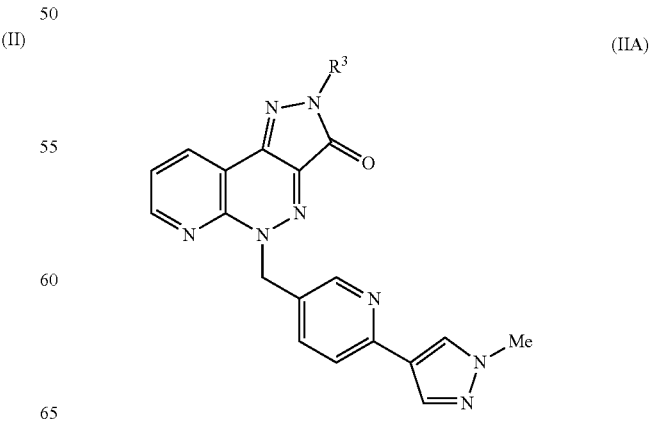

(IIA)

wherein $R^3$ is as described above.

In another embodiment, the compounds of formula (II) are compounds of (IIB)

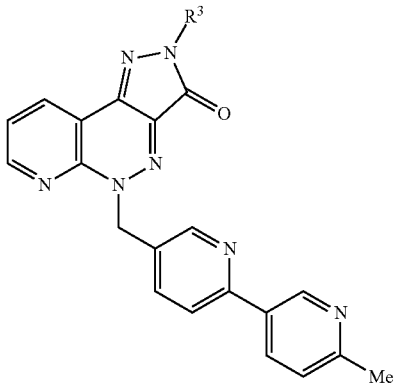

wherein R³ is as described above.

In another embodiment, the compounds of formula (II) are compounds of (IIC)

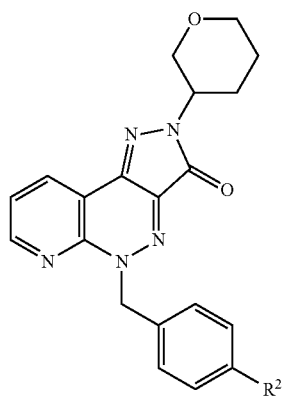

wherein R² is as described above.

In another sub-genus within the genus of compounds of formula (I), there are compounds of formula (III):

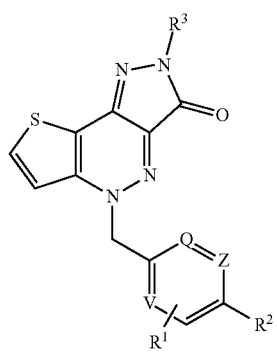

and pharmaceutically acceptable salts thereof, wherein V, Q, Z, $R^1$, R2 and R3 are as described above.

In particular embodiments of the compounds of formula (III), V and Q are CH and Z is N.

In other embodiments of the compounds of formula (III), each of V, Q and Z are CH.

In particular embodiments of the compounds of formula (III), $R^1$ is not present.

In particular embodiments of the compounds of formula (III), $R^2$ is optionally substituted heteroaryl. Exemplary $R^2$ heteroaryl groups include groups having five or six ring atoms, where one or two of the ring atoms is nitrogen and the others are all carbon (e.g., pyrazole or pyridine). Additional heteroaryl groups are groups having five or six ring atoms, having one nitrogen and one sulfur ring atoms, and the others are all carbon (e.g., thiazole).

In other embodiments, $R^2$ is optionally substituted aryl (for example, phenyl)

In still other embodiments, $R^2$ is halogen (suitably fluoro or chloro).

In particular embodiments of the compounds of formula (III), $R^3$ is optionally substituted aryl (suitably, phenyl). Typically, the $R^3$ phenyl group is substituted with one or more $C_{1-6}$ alkyl, and/or with one or more halogen (suitably, fluoro or chloro).

In other embodiments, $R^3$ is heteroaryl. Exemplary $R^3$ heteroaryl groups include groups having five or six ring atoms, where one or two of the ring atoms is nitrogen and the others are all carbon (e.g., pyrazole or pyridine).

In other embodiments, $R^3$ is cycloalkyl (suitably, cyclopentyl or cyclohexyl). Typically, the $R^3$ heterocyclic group is unsubstituted or substituted with hydroxy. For example, $R^3$ may be

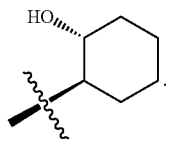

In other embodiments, $R^3$ is heterocyclic (suitably, tetrahydropyran). Typically, the $R^3$ heterocyclic group is unsubstituted or substituted with hydroxy. For example, $R^3$ may be:

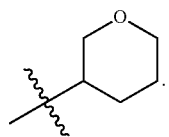

In one embodiment, the compounds of formula (III) are compounds of formula (IIIA):

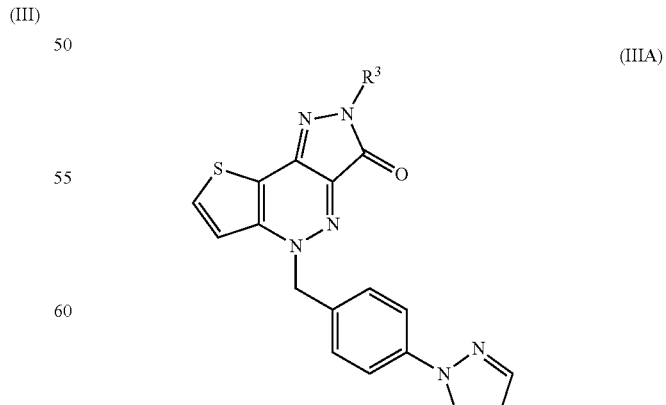

or a pharmaceutically acceptable salt thereof, wherein $R^3$ is as defined above.

Specific embodiments of formula (I) are described herein as Examples 1-39, such as 2-(2,3-Dimethylphenyl)-5-{[6-(1-methyl-1H-pyrazol-4-yl)pyridin-3-yl]methyl}-2,5-dihydro-3H-pyrazolo[4,3-c]pyrido[3,2-e]pyridazin-3-one;

5-[(6-Chloropyridin-3-yl)methyl]-2-(2,3-dimethylphenyl)-2,5-dihydro-3H-pyrazolo[4,3-c]pyrido[3,2-e]pyridazin-3-one;

2-(2,3-Dimethylphenyl)-5-[(6'-methyl-2,3'-bipyridin-5-yl)methyl]-2,5-dihydro-3H-pyrazolo[4,3-c]pyrido[3,2-e]pyridazin-3-one;

2-(2-Fluoro-3-methylphenyl)-5-[(6'-methyl-2,3'-bipyridin-5-yl)methyl]-2,5-dihydro-3H-pyrazolo[4,3-c]pyrido[3,2-e]pyridazin-3-one;

(±)-2-(trans-2-Hydroxycyclohexyl)-5-[(6'-methyl-2,3'-bipyridin-5-yl)methyl]-2,5-dihydro-3H-pyrazolo[4,3-c]pyrido[3,2-e]pyridazin-3-one;

(±)-5-[(6'-Methyl-2,3'-bipyridin-5-yl)methyl]-2-(tetrahydro-2H-pyran-3-yl)-2,5-dihydro-3H-pyrazolo[4,3-c]pyrido[3,2-e]pyridazin-3-one;

(±)-5-{[4-(1H-Pyrazol-1-yl)phenyl]methyl}-2-(tetrahydro-2H-pyran-3-yl)-2,5-dihydro-3H-pyrazolo[4,3-c]pyrido[3,2-e]pyridazin-3-one;

(±)-5-{[4-(6-Methylpyridin-3-yl)phenyl]methyl}-2-(tetrahydro-2H-pyran-3-yl)-2,5-dihydro-3H-pyrazolo[4,3-c]pyrido[3,2-e]pyridazin-3-one;

(±)-2-(Tetrahydro-2H-pyran-3-yl)-5-{[4-(1,3-thiazol-4-yl)phenyl]methyl}-2,5-dihydro-3H-pyrazolo[4,3-c]pyrido[3,2-e]pyridazin-3-one;

(±)-5-{[4-(6-Hydroxypyridin-3-yl)phenyl]methyl}-2-(tetrahydro-2H-pyran-3-yl)-2,5-dihydro-3H-pyrazolo[4,3-c]pyrido[3,2-e]pyridazin-3-one;

2-(2-Methylphenyl)-5-{[4-(1H-pyrazol-1-yl)phenyl]methyl}-2,5-dihydro-3H-pyrazolo[4,3-c]thieno[2,3-e]pyridazin-3-one;

(±)-5-{[4-(1H-Pyrazol-1-yl)phenyl]methyl}-2-(tetrahydro-2H-pyran-3-yl)-2,5-dihydro-3H-pyrazolo[4,3-c]thieno[2,3-e]pyridazin-3-one;

(±)-5-{[4-(6-Methylpyridin-3-yl)phenyl]methyl}-2-(tetrahydro-2H-pyran-3-yl)-2,5-dihydro-3H-pyrazolo[4,3-c]thieno[2,3-e]pyridazin-3-one;

(±)-5-{[4-(2-Methylpyridin-4-yl)phenyl]methyl}-2-(tetrahydro-2H-pyran-3-yl)-2,5-dihyrdo-3H-pyrazolo[4,3-c]thieno[2,3-e]pyridazin-3-one;

and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II) and (III), or a pharmaceutically acceptable salt thereof.

The invention is also directed to the use of a compound of formulae (II) and (III), for treating a disease or disorder in which the M1 receptor is involved, such as Alzheimer's Disease, cognitive impairment, schizophrenia, pain disorders and sleep disorders, by administering to the patient a compound of formulae (II) and (III), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formulae (II) and (III), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formulae (II) and (III), or a pharmaceutically acceptable salt thereof, with a pharmaceutically acceptable carrier.

Where a variable occurs more than once in any of formulae (II) and (III), or in a substituent thereof, the individual occurrences of that variable are independent of each other, unless otherwise specified.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

As used herein, the term "heteroaryl," by itself or as part of another substituent, means a cyclic or polycyclic group having from five to twelve ring atoms selected from C, N, O and S, wherein at least one ring heteroatom is O, N or S, and wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "heterocyclic," by itself or as part of another substituent, means a non-aromatic cylic or polycyclic group having from three to twelve ring atons selected from C, N, O or S, at least one of which is N, O or S. Suitable non-aromatic heterocyclic groups for use in the invention include piperidinyl, piperazinyl, morpholinyl, thiomorpholinyl, tetrahydropyranyl, tetrahydrofuranyl and tetrahyropyrazopyrimidine. Heterocyclic groups for use in the invention have three to twelve ring atoms. Preferred heterocyclic groups have from five to eight ring atoms. More preferred heterocyclic groups have from five to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Preferably, the substituent is bonded to a ring carbon atom. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (III).

Formulae (I) to (III) are shown above without a definite stereochemistry. The present invention includes all stereoisomers of formulae (I) to (III), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

Specific embodiments of the compounds of the invention, and methods of making them, are described in the Examples herein.

The term "substantially pure" means that the isolated material is at least 90% pure, and preferably 95% pure, and even more preferably 99% pure as assayed by analytical techniques known in the art.

As used herein, the term "muscarinic M1 receptor " refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and *Mol Pharmacol*, 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I) to (III) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the present invention provides a method for treating schizophrenia or psychosis comprising administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno- synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists, such as ABT089, SSR180711 and MEM63908; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβoligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT 101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; $GABA_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; O3-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SP1860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSR1") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists and dopamine receptor agonists such as alentemol, bromocriptine, fenoldopam, lisuride, naxagolide, pergolide and pramipexole.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight, In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 025 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the schemes and examples herein. Starting materials are made according to procedures known in the art or as illustrated herein. The following examples are provided so that the invention might be more fully understood.

The following examples are provided to illustrate the invention and are not to be construed as limiting the scope of the invention in any manner.

Generic Scheme 1:

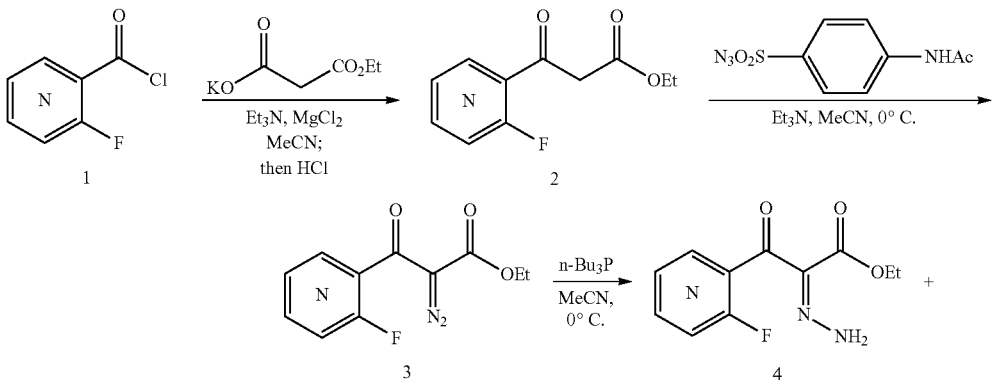

-continued
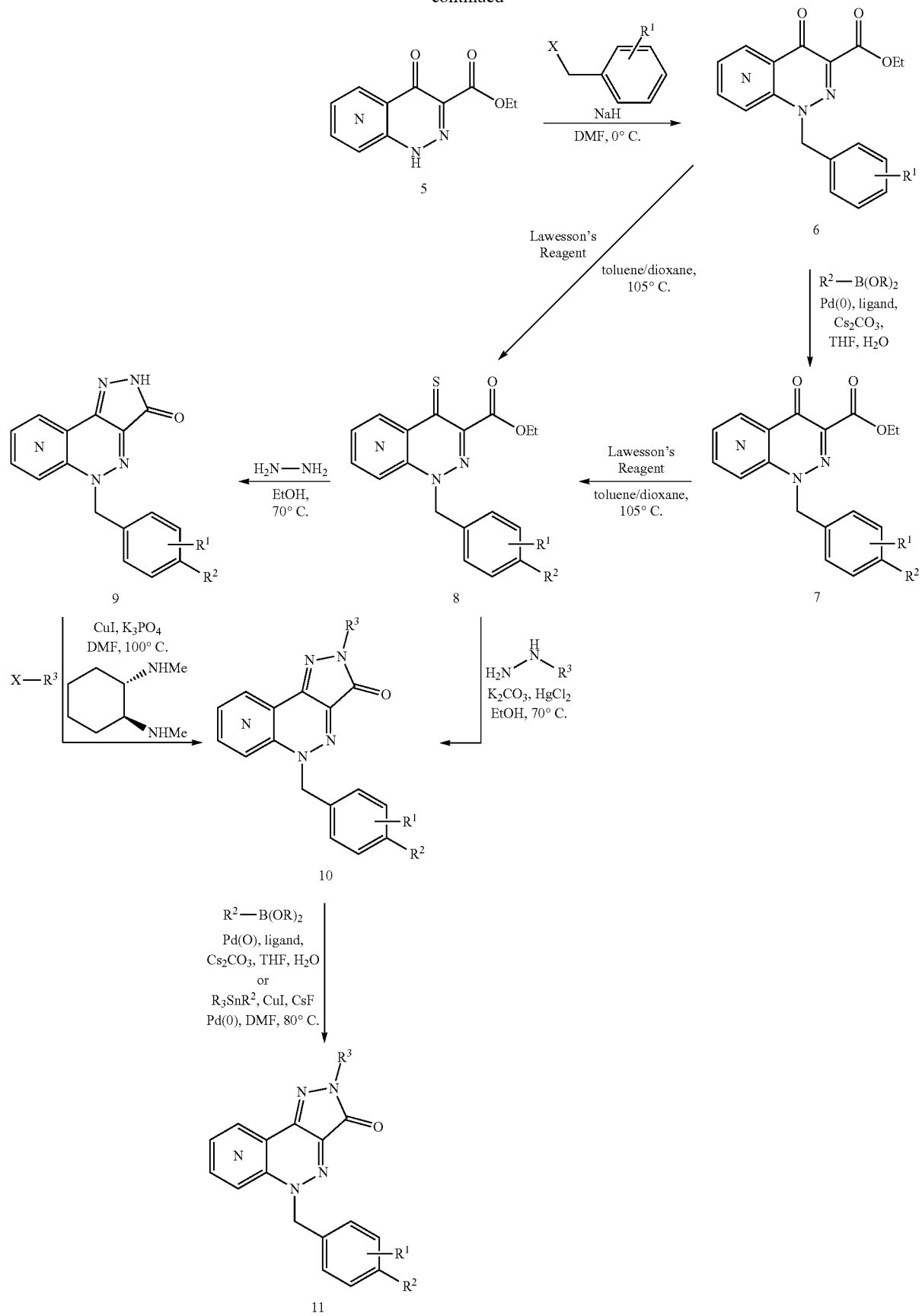

Compound 1 is a commercially available compound and can be converted to the β-keto ester 2 via the enolate derived from potassium ethyoxymalonate. Conversion to the diazo 3 can be accomplished in the presence of a base, such as triethylamine, and 4-acetamidobenzenesulfonyl azide. Treatment with a reducing agent, such as tri-n-butylphosphine, can afford a mixture, or either the hydrazone 4 or cyclized compound 5. Alkylation of either 4 or 5 with a benzylic halide in the presence of a suitable base, like sodium hydride, can afford 6. If appropriately substituted (i.e., $R^1$=Cl, Br, or I), 6 can undergo palladium-mediated functionalization to 7 and then 6 or 7 can be converted to the thioketone 8 via Lawesson's Reagent at elevated temperatures. Reaction of the thioketone with hydrazine can afford 9, which may undergo copper-mediated N-arylation to afford 10 or 10 could be directly obtained by treatment of 8 with a suitably substituted hydrazine, in the presence of a base, such as potassium carbonate, and in the presence of a suitable activator, like mercury(II) chloride. Further functionalization of 10 can also be accomplished to afford compound 11.

Generic Scheme 2:

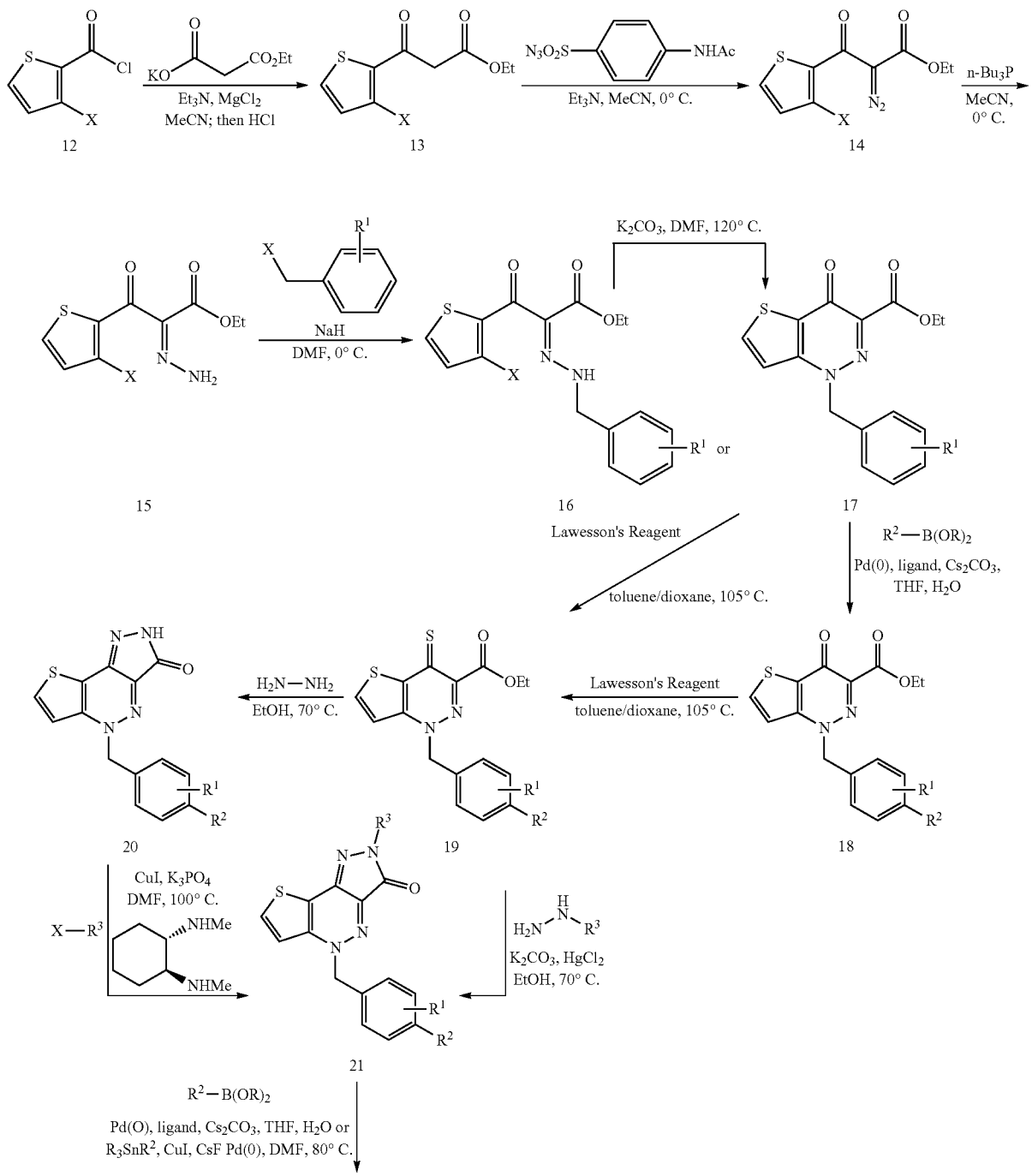

-continued

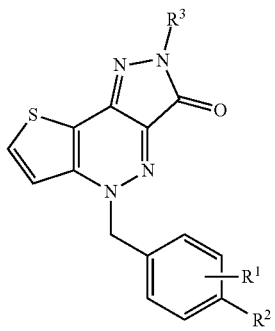

22

Compound 12 (X=Cl or F) can be obtained or readily prepared from commercial sources and converted to the β-keto ester 13 via the enolate derived from potassium ethyoxymalonate. Conversion to the diazo 14 can be accomplished in the presence of a base, such as triethylamine, and 4-acetamidobenzenesulfonyl azide. Treament with a reducing agent, such as tri-n-butylphosphine, can afford hydrazone 15. Alkylation with a suitably substituted benzylic halide in the presence of a suitable base, like sodium hydride, can afford either 16 or 17; compound 16 can undergo cyclization to 17 in the presence of a suitable base, such as potassium carbonate, in an appropriate solvent, such as N,N-dimethylformamide, at elevated temperature. If appropriately substituted (i.e., $R^1$=Cl, Br, or I), 17 can undergo palladium-mediated functionalization to 18 and then 17 or 18 can be converted to the thioketone 19 via Lawesson's Reagent at elevated temperatures. Reaction of the thioketone with hydrazine can afford 20, which can undergo copper-mediated N-arylation to afford 21 or 21 can be directly obtained by treatment of 19 with a suitably substituted hydrazine, in the presence of a base, such as potassium carbonate, and in the presence of a suitable activator, like mercury(II) chloride. Further functionalization of 21 can also be accomplished to afford compound 22.

The following examples are provided to illustrate the invention and are not to be construed as limiting the scope of the invention in any manner.

EXAMPLE 1

2-(2,3-Dimethylphenyl)-5-{[6-(1-methyl-1H-pyrazol-4-yl)pyridin-3-yl]methyl}-2,5-dihydro-3H-pyrazolo[4,3-c]pyrido[3,2-e]pyridazin-3-one

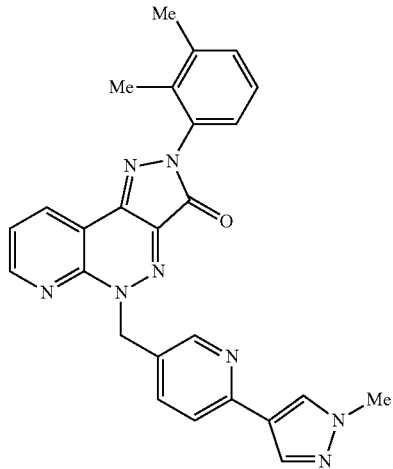

Step 1: Preparation of 2-fluoropyridine-3-carbonyl choride: 2-Fluoropyridine-3-carboxylic acid (5.02 g, 35.6 mmol) was suspended in dichloromethane (100 mL), treated with thionyl chloride (13.0 mL, 178 mmol, 5 equiv) and N,N-dimethylformamide (0.138 mL, 1.78 mmol, 0.05 equiv) and placed into a preheated oil bath at 45° C. for 2 hours. The mixture was cooled to ambient temperature, concentrated in vacuo and the residue was concentrated from toluene (2×50 mL), providing the titled compound.

Step 2: Preparation of ethyl 3-(2-fluoropyridine-3-yl)-3-oxopropanoate: Potassium 3-(ethoxy)-3-oxopropanoate (6.06 g, 35.6 mmol) was suspended in acetonitrile (100 mL), cooled to 0° C. and treated successively with triethylamine (4.96 mL, 35.6 mmol, 1 equiv) and anhydrous magnesium(II) chloride (3.39 g, 35.6 mmol, 1 equiv). The ice bath was removed and the mixture was warmed to ambient temperature and stirred for 2.5 hours. An acetonitrile (5 mL) solution of 2-fluoropyridine-3-carbonyl choride (5.68 g, 35.6 mmol) was added and the mixture was stirred for 72 hours at ambient temperature. The mixture was concentrated in vacuo and the residue was concentrated from toluene (1×75 mL). The residue was suspended in toluene (50 mL), cooled to 0° C. and treated with hydrochloric acid (20 mL, 12 N aqueous). After 15 minutes, the mixture was warmed to ambient temperature and stirred for an additional 45 minutes. The mixture was poured into water (50 mL) and extracted with ethyl acetate (3×75 mL). The combined organic extracts were dried with sodium sulfate, filtered and concentrated in vacuo. The residue was purified by silica gel gradient chromatography (100:0 to 1:1; hexanes:ethyl acetate), providing the titled compound.

Step 3: Preparation of ethyl 2-diazo-3-(2-fluoropyridin-3-yl)-3-oxopropanoate: Ethyl 3-(2-fluoropyridine-3-yl)-3-oxopropanoate (1.42 g, 6.71 mmol) was dissolved in anhydrous acetonitrile (20 mL), treated with triethylamine (0.781 mL, 1.15 equiv) and cooled to 0° C. To the mixture was added the 4-acetamidobenzenesulfonyl azide (1.77 g, 1.1 equiv) and after stirring 0° C. for 1 hour, the mixture was treated with sodium hydroxide (10 mL, 1 N aqueous). The mixture was poured into sodium carbonate (50 mL, aqueous saturated) and water (200 mL) and extracted with ethyl acetate (2×250 mL). The combined organic extracts were washed once with brine (50 mL), dried with sodium sulfate, filtered and concentrated in vacuo. The residue was purified by silica gel gradient chromatography (100:0 to 70:30; hexanes:ethyl acetate), providing the titled compound as a light yellow oil.

Step 4: Preparation of ethyl 2-(2Z)-3-(2-fluoropyridin-3-yl)-2-hydrazono-3-oxopropanoate: Ethyl 2-diazo-3-(2-fluoropyridin-3-yl)-3-oxopropanoate (1.39 g, 5.86 mmol) was dissolved in tetrahydrofuran (10 mL), cooled to 0° C. and treated with tri-n-butylphosphine (1.46 mL, 5.86 mmol, 1 equiv). After 30 minutes, the mixture was concentrated in vacuo and the residue was purified by silica gel gradient chromatography (100:0 to 50:50; hexanes:ethyl acetate), providing the titled compound as a white solid.

Step 5: Preparation of (6-bromopyridin-3-yl)methyl methanesulfonate: (6-Bromopyridin-3-yl)methanol (2.45 g, 13.0 mmol) was dissolved in dichloromethane (20 mL), cooled to 0° C. and treated successively with N,N-diisopropylethylamine (2.73 mL, 15.6 mmol, 1.2 equiv) and methanesulfonyl chloride (1.17 mL, 15.0 mmol, 1.15 equiv). After stirring for 30 minutes, the mixture was treated with ammonium chloride (10 mL, aqueous saturated) and warmed to ambient temperature. The mixture was poured into water (100 mL) and extracted with ethyl acetate (2×100 mL). The combined organic extracts were dried with sodium sulfate, filtered and concentrated in vacuo, providing the titled compound.

Step 6: Preparation of ethyl 1-[(6-bromopyridin-3-yl)methyl]-4-oxo-1,4-dihydropyrido[2,3-c]pyridazine-3-carboxylate: Ethyl 2-(2Z)-3-(2-fluoropyridin-3-yl)-2-hydrazono-3-oxopropanoate (308 mg, 1.29 mmol) and (6-bromopyridin-3-yl)methyl methanesulfonate (360 mg, 1.35 mmol, 1.05 equiv) were dissolved in N,N-dimethylformamide (7 mL), the mixture was degassed and cooled to 0° C. The mixture was treated with sodium hydride (103 mg, 2.58 mmol, 2 equiv, 60% dispersion in mineral oil), stirred at 0° C. for 45 minutes, after which additional sodium hydride (50 mg, 1.29 mmol, 1 equiv, 60% dispersion in mineral oil) was added. The mixture was warmed to ambient temperature, stirred for an additional 30 minutes and treated with sodium bicarbonate (10 mL, aqueous saturated). The mixture was poured into water (75 mL) and extracted with ethyl acetate (2×75 mL). The combined organic extracts were dried with sodium sulfate, filtered and concentrated in vacuo. The residue was purified by silica gel gradient chromatography (100:0 to 0:100; hexanes:ethyl acetate), providing the titled compound.

Step 7: Preparation of ethyl 1-{[6-(1-methyl-1H-pyrazol-4-yl)pyridiny-3-yl]methyl}-4-oxo-1,4-dihydropyrido[2,3-c]pyridazine-3-carboxylate: Ethyl 1-[(6-bromopyridin-3-yl)methyl]-4-oxo-1,4-dihydropyrido[2,3-c]pyridazine-3-carboxylate (212 mg, 0.545 mmol) and 1-methyl-4-(4,4,5,5-tetramethyl-1,3,2-dioxaborolan-2-yl)-1H-pyrazole (193 mg, 0.926 mmol) were suspended in tetrahydrofuran (10 mL) and treated with an aqueous solution (1 mL) of cesium carbonate (355 mg, 1.09 mmol, 2 equiv). The mixture was degassed, treated with bis(tri-tert-butylphosphine)palldium(0) (55.7 mg, 0.109 mmol, 0.2 equiv) and placed into a preheated oil bath at 80° C. for 1 hour. The mixture was cooled to ambient temperature, poured into sodium bicarbonate (75 mL, aqueous saturated) and extracted with ethyl acetate (2×100 mL). The combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound.

Step 8: Preparation of ethyl 1-{[4-(1-methyl-1H-pyrazol-4-yl)pyridiny-3-yl]methyl}-4-thioxo-1,4-dihydropyrido[2,3-c]pyridazine-3-carboxylate: Ethyl 1-{[6-(1-methyl-1H-pyrazol-4-yl)pyridin-3-yl]methyl}-4-oxo-1,4-dihydropyrido[2,3-c]pyridazine-3-carboxylate (127 mg, 0.325 mmol) was suspended in dioxane (6 mL) and toluene (6 mL) and placed into an oil bath preheated to 100° C. To the mixture was added 2,4-bis-(4-methoxyphenyl)-1,3-dithia-2,4-diphosphetane 2,4-disulfide (Lawesson's Reagent, 132 mg, 0.325 mmol, 1 equiv) portionwise over 5 minutes. After stirring for 30 minutes at 100° C., the mixture was cooled to ambient temperature and concentrated in vacuo. The residue was purified by silica gel gradient chromatography (100:0 to 0:100; hexanes:ethyl acetate containing 10% methanol), providing the titled compound as a dark green foam.

Step 9: Preparation of 5-{[6-(1-methyl-1H-pyrazol-4-yl)pyridin-3-yl]methyl}-2,5-dihydro-3H-pyrazolo[4,3-c]pyrido[3,2-e]pyridazin-3-one: Ethyl 1-{[4-(1-methyl-1H-pyrazol-4-yl)pyridiny-3-yl]methyl}-4-thioxo-1,4-dihydropyrido[2,3-c]pyridazine-3-carboxylate (200 mg, 0.492 mmol) was suspended in ethanol (10 mL), treated with hydrazine (1.00 mL, 31.9 mmol, 65 equiv) and placed into a preheated oil bath at 70° C. for 15 minutes. The mixture was cooled to ambient temperature and concentrated in vacuo. The residue was concentrated toluene (1×15 mL), providing the titled compound as a deep red solid.

Step 10: Preparation of 2-(2,3-dimethylphenyl)-5-{[6-(1-methyl-1H-pyrazol-4-yl)pyridin-3-yl]methyl}-2,5-dihydro-3H-pyrazolo[4,3-c]pyrido[3,2-e]pyridazin-3-one: 5-{[6-(1-Methyl-1H-pyrazol-4-yl)pyridin-3-yl]methyl}-2,5-dihydro-3H-pyrazolo[4,3-c]pyrido[3,2-e]pyridazin-3-one (50 mg, 0.14 mmol), copper(I) iodide (27 mg, 0.14 mmol, 1 equiv), potassium phosphate (0.18 g, 0.84 mmol, 6 equiv), (±)-trans-N,N'-bismethyl-1,2-cyclohexanediamine (59 mg, 0.42 mmol, 3 equiv) and 3-iodo-ortho-xylene (59 µL, 0.42 mmol, 3 equiv) were combined in degassed N,N-dimethylformamide (2.5 mL) and placed into an oil bath preheated to 110° C. for 30 minutes. The mixture was cooled to ambient temperature, poured into sodium bicarbonate (25 mL, aqueous saturated) and extracted with ethyl acetate (3×50 mL). The combined organic extracts were dried with sodium sulfate, filtered and concentrated in vacuo. The residue was purified by silica gel gradient chromatography (100:0 to 0:100; hexanes:ethyl acetate containing 10% methanol), providing the titled compound: $^1$H-NMR (400 MHz, CDCl$_3$) δ 8.83 (1H, d, J=2.2 Hz), 8.78 (1H, dd, J=4.6, 1.7 Hz), 8.54 (1H, dd, J=8.0, 1.9 Hz), 7.92 (1H, dd, J=7.9, 2.2 Hz), 7.91 (1H, s), 7.89 (1H, s), 7.51 (1H, dd, J=8.0, 4.6 Hz), 7.41 (1H, d, J=8.3 Hz), 7.26 (1H, br s), 7.23-7.21 (2H, m), 5.96 (2H, s), 3.94 (3H, s), 2.36 (3H, s), 2.16 (3H, s) ppm; high resolution mass spectrometry (ES+) m/z 463.1986 [(M+H)$^+$; calculated for C$_{26}$H$_{23}$N$_8$O: 463.1989].

The following compounds of formula (IIA) were prepared according to the general procedure described in Example 1, substituting the appropriate iodide for 3-iodo-ortho-xylene (Step 10). The starting materials are either commercially available, known in the literature or may be prepared from commercially available reagents using conventional reactions well known in the art.

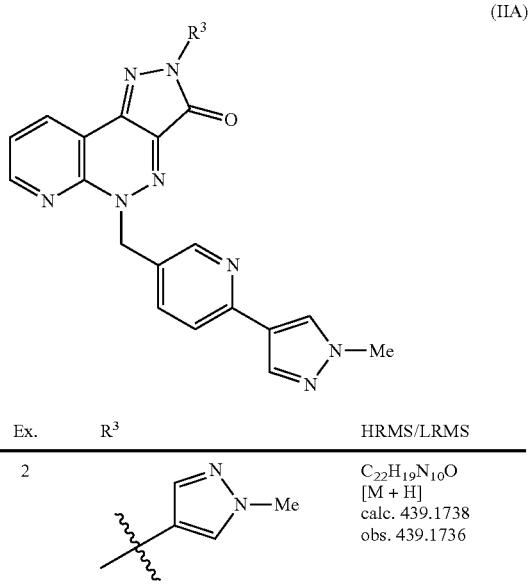

| Ex. | R$^3$ | HRMS/LRMS |
|---|---|---|
| 2 | ![structure] | C$_{22}$H$_{19}$N$_{10}$O [M + H] calc. 439.1738 obs. 439.1736 |

-continued

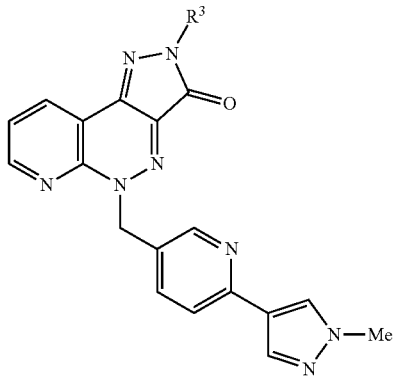

(IIA)

| Ex. | R³ | HRMS/LRMS |
|---|---|---|
| 3 | ![structure](Me, F on phenyl) | C₂₅H₂₀FN₈O [M + H] calc. 467.1739 obs. 467.1751 |

EXAMPLE 4

5-[(6-Chloropyridin-3-yl)methyl]-2-(2,3-dimethylphenyl)-2,5-dihydro-3H-pyrazolo[4,3-c]pyrido[3,2-e]pyridazin-3-one

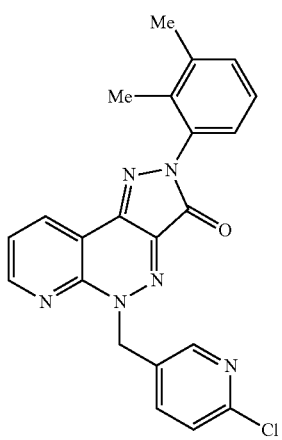

Step 1: Preparation of ethyl 1-[(6-bromopyridin-3-yl)methyl]-4-thioxo-1,4-dihydropyrido[2,3-c]pyridazine-3-carboxylate: Ethyl 1-[(6-bromopyridin-3-yl)methyl]-4-oxo-1,4-dihydropyrido[2,3-c]pyridazine-3-carboxylate [(Example 1, Step 6) 580 mg, 1.49 mmol] was suspended in toluene (5 mL) and dioxane (5 mL), placed into an oil bath preheated to 110° C. and treated in one portion with Lawesson's Reagent (603 mg, 1.49 mmol, 1 equiv). After stirring for 30 minutes, the mixture was cooled to ambient temperature and concentrated in vacuo. The residue was purified by silica gel gradient chromatography (100:0 to 50:50; hexanes:ethyl acetate), providing the titled compound.

Step 2: Preparation of 5-[(6-bromopyridin-3-yl)methyl]-2,5-dihydro-3H-pyrazolo[4,3-c]pyrido[3,2-e]pyridazin-3-one: Ethyl 1-[(6-bromopyridin-3-yl)methyl]-4-thioxo-1,4-dihydropyrido[2,3-c]pyridazine-3-carboxylate (120 mg, 0.296 mmol) was suspended in ethanol (15 mL), treated with hydrazine (1.00 mL, 31.9 mmol, 107 equiv) and placed into an oil bath preheated to 80° C. for 1 hour. The mixture was cooled to ambient temperature and concentrated in vacuo, providing the titled compound.

Step 3: Preparation of 5-[(6-chloropyridin-3-yl)methyl]-2-(2,3-dimethylphenyl)-2,5-dihydro-3H-pyrazolo[4,3-c]pyrido[3,2-e]pyridazin-3-one: 5-[(6-bromopyridin-3-yl)methyl]-2,5-dihydro-3H-pyrazolo[4,3-c]pyrido[3,2-e]pyridazin-3-one (106 mg, 0.297 mmol), copper(I) iodide (56.5 mg, 0.297 mmol, 1 equiv), potassium phosphate (378 mg, 1.78 mmol, 6 equiv), (±)-trans-N,N'-bismethyl-1,2-cyclohexanediamine (127 mg, 0.890 mmol, 3 equiv) and 3-iodo-ortho-xylene (126 μL, 0.890 mmol, 3 equiv) were combined in degassed N,N-dimethylformamide (2.5 mL) and placed into an oil bath preheated to 110° C. for 1 hour. The mixture was cooled to ambient temperature, poured into sodium bicarbonate (25 mL, aqueous saturated) and extracted with ethyl acetate (3×75 mL). The combined organic extracts were dried with sodium sulfate, filtered and concentrated in vacuo. The residue was purified by silica gel gradient chromatography (100:0 to 0:100; hexanes:ethyl acetate), providing the titled compound as a deep red solid: ¹H-NMR (400 MHz, CDCl₃) δ 8.75 (1H, dd, J=4.6, 1.8 Hz), 8.69 (1H, d, J=2.5 Hz), 8.54 (1H, dd, J=8.0, 1.9 Hz), 7.92 (1H, dd, J=8.3, 2.5 Hz), 7.52 (1H, dd, J=8.0, 4.6 Hz), 7.24-7.21 (3H, m), 5.94 (2H, s), 2.36 (3H, s), 2.16 (3H, s) ppm; high resolution mass spectrometry (ES+) m/z 417.1234 [(M+H)⁺; calculated for C₂₂H₁₈ClN₆O: 417.1225].

EXAMPLE 5

2-(2,3-Dimethylphenyl)-5-[(6'-methyl-2,3'-bipyridin-5-yl)methyl]-2,5-dihydro-3H-pyrazolo[4,3-c]pyrido[3,2-e]pyridazin-3-one

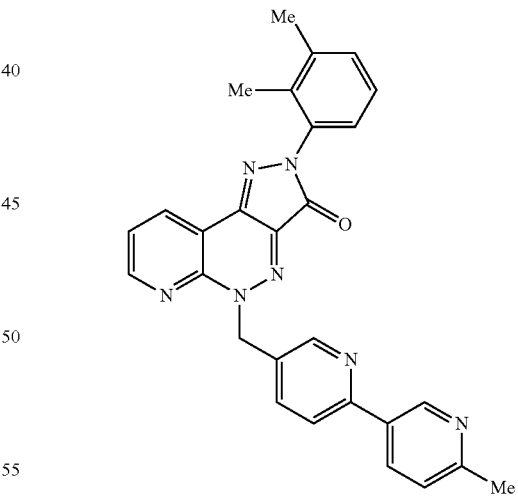

Step 1: Preparation of ethyl 4-oxo-1,4-dihydropyrido[2,3-c]pyridazine-3-carboxylate: Ethyl 2-diazo-3-(2-fluoropyridin-3-yl)-3-oxopropanoate [(Example 1, Step 3), 1.39 g, 5.86 mmol] was dissolved in tetrahydrofuran (10 mL), cooled to 0° C. and treated with tri-n-butylphosphine (1.46 mL, 5.86 mmol, 1 equiv). After 30 minutes, the mixture was concentrated in vacuo and the residue was purified by silica gel gradient chromatography (100:0 to 0:100; hexanes:ethyl acetate), providing ethyl 2-(2Z)-3-(2-fluoropyridin-3-yl)-2-hydrazono-3-oxopropanoate, as well as the titled compound as a white solid.

Step 2: Preparation of ethyl 1-[(6-chloropyridin-3-yl)methyl]-4-oxo-1,4-dihydropyrido[2,3-c]pyridazine-3-carboxylate: Ethyl 4-oxo-1,4-dihydropyrido[2,3-c]pyridazine-3-carboxylate (1.00 g, 4.56 mmol) and 2-chloro-5-(chloromethyl)pyridine (813 mg, 5.02 mmol, 1.1 equiv) were combined in degassed N,N-dimethylformamide and cooled to 0° C. Sodium hydride (219 mg, 5.47 mmol, 1.2 equiv) was added portionwise over 5 minutes and the mixture was stirred for an additional 1 hour at 0° C. The mixture was warmed to ambient temperature, stirred for 1 hour and poured into sodium bicarbonate (150 mL, aqueous saturated). The aqueous layer was extracted with ethyl acetate (2×150 mL) and the combined organic extracts were dried with sodium sulfate, filtered and concentrated in vacuo. The residue was purified by silica gel gradient chromatography (100:0 to 0:100; hexanes:ethyl acetate), providing the titled compound as a white solid.

Step 3: Preparation of ethyl 1-[(6-chloropyridin-3-yl)methyl]-4-thioxo-1,4-dihydropyrido[2,3-c]pyridazine-3-carboxylate: Ethyl 1-[(6-chloropyridin-3-yl)methyl]-4-oxo-1,4-dihydropyrido[2,3-c]pyridazine-3-carboxylate (490 mg, 1.42 mmol) was suspended in toluene (5 mL) and dioxane (5 mL) and placed into a preheated oil bath at 110° C. The mixture was treated with Lawesson's Reagent (316 mg, 0.782 mmol, 0.55 equiv) portionwise over 45 minutes and stirred for an addition 30 minutes at 110° C. The mixture was cooled to ambient temperature and concentrated in vacuo. The residue was purified by silica gel gradient chromatography (100:0 to 50:50; hexanes:ethyl acetate), providing the titled compound as a brown foam.

Step 3: Preparation of 5-[(6-chloropyridin-3-yl)methyl]-2-(2,3-dimethylphenyl)-2,5-dihydro-3H-pyrazolo[4,3-c]pyrido[3,2-e]pyridazin-3-one (Example 4): Ethyl 1-[(6-chloropyridin-3-yl)methyl]-4-thioxo-1,4-dihydropyrido[2,3-c]pyridazine-3-carboxylate (389 mg, 1.08 mmol), (2,3-dimethylphenyl)hydrazine hydrochloride (279 mg, 1.62 mmol, 1.5 equiv) and potassium carbonate (1.49 g, 10.8 mmol, 10 equiv) were combined and placed into an oil bath preheated to 70° C. for 3 hours. The mixture was cooled to ambient temperature, poured into sodium bicarbonate (150 mL, aqueous saturated) and extracted with ethyl acetate (3×100 mL). The combined organic extracts were washed with brine (1×50 mL), dried with sodium sulfate, filtered and concentrated in vacuo. The residue was purified by silica gel gradient chromatography (100:0 to 0:100; hexanes:ethyl acetate containing 5% methanol), providing the titled compound as a deep red solid.

Step 4: Preparation of 2-(2,3-dimethylphenyl)-5-[(6'-methyl-2,3'-bipyridin-5-yl)methyl]-2,5-dihydro-3H-pyrazolo[4,3-c]pyrido[3,2-e]pyridazin-3-one: 5-[(6-Chloropyridin-3-yl)methyl]-2-(2,3-dimethylphenyl)-2,5-dihydro-3H-pyrazolo[4,3-c]pyrido[3,2-e]pyridazin-3-one [(Example 4), 47 mg, 0.11 mmol], cesium carbonate (92 mg, 0.28 mmol, 2.5 equiv), copper(I) chloride (11 mg, 0.11 mmol, 1 equiv), 2-methyl-5-pyridinylboronic acid (39 mg, 0.28 mmol, 2.5 equiv) and bis(tri-tert-butylphosphine)palladium(0) (11 mg, 0.023 mmol, 0.2 equiv) were combined in tetrahydrofuran (4 mL) and placed into a preheated oil bath at 70° C. After 45 minutes, water (1 mL) was added and after 45 minutes, the mixture was poured into sodium bicarbonate (50 mL) and extracted with ethyl acetate (2×50 mL). The combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound as a deep red solid: $^1$H-NMR (400 MHz, CDCl$_3$) δ 9.04 (1H, d, J=1.4 Hz), 8.89 (1H, d, J=2.3 Hz), 8.79 (1H, dd, J=4,6, 1.7 Hz), 8.55 (1H, dd, J=8.0, 1.8 Hz), 8.18 (1H, dd, J=8.1, 2.3 Hz), 8.03 (1H, dd, J=8.2, 2.2 Hz), 7.70 (1H, d, J=8.2 Hz), 7.52 (1H, dd, J=8.0, 4.6 Hz), 7.27-7.25 (1H, m), 7.24-7.22 (3H, m), 6.02 (2H, s), 2.61 (3H, s), 2.36 (3H, s), 2.16 (3H, s) ppm; high resolution mass spectrometry (ES+) m/z 474.2043 [(M+H)$^+$; calculated for C$_{28}$H$_{24}$N$_7$O: 474.2037].

EXAMPLE 6

2-(2-Fluoro-3-methylphenyl)-5-[(6'-methyl-2,3'-bipyridin-5-yl)methyl]-2,5-dihydro-3H-pyrazolo[4,3-c]pyrido[3,2-e]pyridazin-3-one

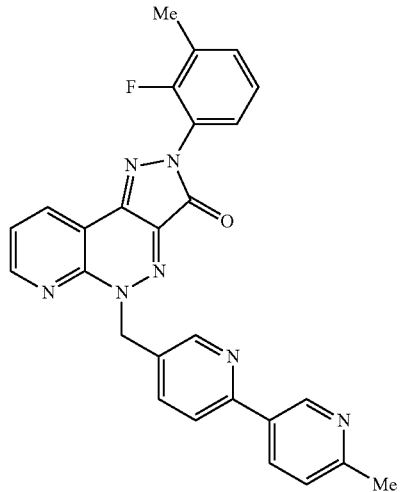

Step 1: Preparation of ethyl 1-[(6-methyl-2,3'-bipyridin-5-yl)methyl]-4-oxo-1,4-dihydropyrido[2,3-c]pyridazine-3-carboxylate: Ethyl 1-[(6-chloropyridin-3-yl)methyl]-4-thioxo-1,4-dihydropyrido[2,3-c]pyridazine-3-carboxylate [(Example 5, Step 3), 335 mg, 0.972 mmol] was dissolved in tetrahydrofuran (15 mL), treated with an aqueous solution (3 mL) of cesium carbonate (792 mg, 2.43 mmol, 2.5 equiv), copper(I) chloride (96.0 mg, 0.972 mmol, 1 equiv), 2-methyl-5-pyridinylboronic acid (333 mg, 2.43 mmol, 2.5 equiv) and bis(tri-tert-butylphosphine)palladium(0) (99.0 mg, 0.194 mmol, 0.2 equiv). The mixture was placed into a preheated oil bath at 70° C. for 2 hours, cooled to ambient temperature, poured into sodium bicarbonate (50 mL, aqueous saturated) and water (100 mL) and then extracted with ethyl acetate (2×75 mL). The combined organic extracts were dried with sodium sulfate, filtered and concentrated in vacuo. The residue was purified by silica gel gradient chromatography (100:0 to 0:100; hexanes:ethyl acetate containing 10% methanol), providing the titled compound as a light yellow solid.

Step 2: Preparation of ethyl 1-[(6-methyl-2,3'-bipyridin-5-yl)methyl]-4-thioxo-1,4-dihydropyrido[2,3-c]pyridazine-3-carboxylate: Ethyl 1-[(6-methyl-2,3'-bipyridin-5-yl)methyl]-4-oxo-1,4-dihydropyrido[2,3-c]pyridazine-3-carboxylate (139 mg, 0.346 mmol) was suspended in dioxane (6 mL) and toluene (3 mL), placed into a preheated oil bath at 100° C. and treated with Lawesson's Reagent (84.0 mg, 0.208 mmol, 0.6 equiv) portionwise over 5 minutes. After stirring for 30 minutes, the mixture was cooled to ambient temperature and concentrated in vacuo. The residue was purified by silica gel gradient chromatography (100:0 to 0:100; hexanes:ethyl acetate containing 5% methanol), providing the titled compound as brownish-green foam.

Step 3: Preparation of 5-[(6'-methyl-2,3'-bipyridin-5-yl)methyl]-2,5-dihydro-3H-pyrazolo[4,3-c]pyrido[3,2-e]pyridazine-3-one: Ethyl 1-[(6-methyl-2,3'-bipyridin-5yl)methyl]-4-thioxo-1,4-dihydropyrido[2,3-c]pyridazine-3-carboxylate (159 mg, 0.381 mmol) was suspended in ethanol (15 mL), placed into a preheated oil bath at 70° C. and treated with hydrazine (0.012 mL, 0.381 mmol, 1 equiv). After 1 hour, the mixture was cooled to ambient temperature, concentrated in vacuo and the residue was concentrated from toluene (2×50 mL), providing the titled compound as a deep red solid.

Step 4: Preparation of 2-(2-fluoro-3-methylphenyl)-5-[(6'-methyl-2,3'-bipyridin-5-yl)methyl]-2,5-dihydro-3H-pyrazolo[4,3-c]pyrido[3,2-e]pyridazin-3-one: 5-[(6'-Methyl-2,3'-bipyridin-5-yl)methyl]-2,5-dihydro-3H-pyrazolo[4,3-c]pyrido[3,2-e]pyridazine-3-one (40 mg, 0.11 mmol), copper (I) iodide (21 mg, 0.11 mmol, 1 equiv), potassium phosphate (0.14 g, 0.65 mmol, 6 equiv), (±)-trans-N,N'-bismethyl-1,2-cyclohexanediamine (46 mg, 0.32 mmol, 3 equiv) and 2-fluoro-1-iodo-3-methylbenzene (64 mg, 0.27 mmol, 2.5 equiv) were combined in degassed N,N-dimethylformamide (2.5 mL) and placed into an oil bath preheated to 110° C. for 45 min. The mixture was cooled to ambient temperature, poured into sodium bicarbonate (100 mL, aqueous saturated) and extracted with ethyl acetate (3×75 mL). The combined organic extracts were washed once with brine (50 mL), dried with sodium sulfate, filtered and concentrated in vacuo. The residue was purified by silica gel gradient chromatography (100:0 to 0:100; hexanes:ethyl acetate containing 10% methanol), providing the titled compound as a red solid: $^1$H-NMR (400 MHz, CDCl$_3$) δ 9.04 (1H, d, J=1.8 Hz), 8.97 (1H, d, J=1.7 Hz), 8.79 (1H, dd, J=4.6, 1.9 Hz), 8.56 (1H, dd, J=8.0, 1.8 Hz), 8.18 (1H, dd, J=8.1, 2.2 Hz), 8.01 (1H, dd, J=8.2, 2.3 Hz), 7.70 (1H, dd, J=8.2, 0.6 Hz), 7.52 (1H, dd, J=8.0, 4.6 Hz), 7.41-7.37 (1H, ), 7.27-7.22 (2H, m), 7.15 (1H, ap t, J=7.9 Hz), 6.01 (2H, s), 2.60 (3H, s), 2.36 (1H, J=2.0 Hz) ppm; high resolution mass spectrometry (ES+) m/z 478.1783 [(M+H)$^+$; calculated for C$_{27}$H$_{21}$FN$_7$O: 478.1786].

The following compound of formula (IIB) were prepared according to the general procedure described in Example 6, substituting 6-chloro-3-iodo-2-methylpyridine for 2-fluoro-1-iodo-3-methylbenzene (Step 4). The starting materials are either commercially available, known in the literature or may be prepared from commercially available reagents using conventional reactions well known in the art.

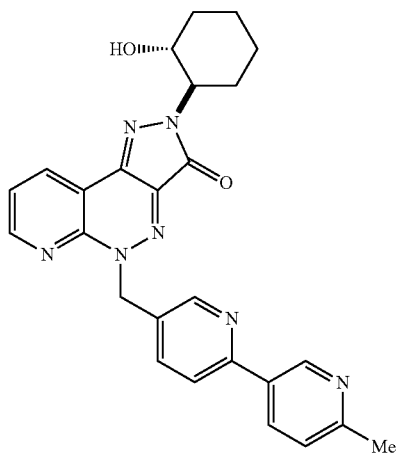

(IIB)

| Ex. | R$^3$ | HRMS/LRMS |
|---|---|---|
| 7 | Me-N-Cl (structure) | C$_{26}$H$_{20}$ClN$_8$O [M + H] calc. 495.1443 obs. 495.1450 |

EXAMPLE 8

(±)-2-(trans-2-Hydroxycyclohexyl)-5-[(6'-methyl-2,3'-bipyridin-5-yl)methyl]-2,5-dihydro-3H-pyrazolo[4,3-c]pyrido[3,2-e]pyridazin-3-one Ethyl 1-[(6-methyl-2,3'-bipyridin-5-yl)methyl]-4-thioxo-1,4-dihydropyrido[2,3-c]pyridazine-3-carboxylate [(Example 6, Step 2), 47 mg, 0.11 mmol], (±)-trans-2-hydrazinocyclohexanol (44 mg, 0.34 mmol, 3 equiv), potassium carbonate (0.16 g, 1.1 mmol, 10 equiv) and mercury(II) chloride (31 mg, 0.11 mmol, 1 equiv) were combined in ethanol (10 mL) at ambient temperature and after 5 minutes, the mixture was warmed to 70° C. for 3 h. The mixture was cooled to ambient temperature, poured into sodium bicarbonate (100 mL, aqueous saturated) and extracted with ethyl acetate (3×75 mL). The combined organic extracts were dried with sodium sulfate, filtered and concentrated in vacuo. The residue was purified by preparative TLC (eluting with ethyl acetate containing 10% methanol), providing the titled compound: $^1$H-NMR (400 MHz, CDCl$_3$) δ 9.02 (1H, d, J=2.1 Hz), 8.93 (1H, d, J=2.0 Hz), 8.75 (1H, dd, J=4.6, 1.8 Hz), 8.52 (1H, dd, J=8.1, 1.8 Hz), 8.16 (1H, dd, J=8.2, 2.4 Hz), 7.97 (1H, dd, J=8.3, 2.3 Hz), 7.66 (1H, dd, J=8.2, 0.6 Hz), 7.50 (1H, dd, J=8.0, 4.6 Hz), 7.23 (1H, d, J=8.0 Hz), 6.0 (1H, d, J=14.3 Hz), 5.96 (1H, d, J=14.3 Hz), 4.30 (1H, ddd, J=11.7, 9.8, 4.1 Hz), 4.07-4.01 (1H, m,), 2.60 (3H, s), 2.20 (1H, br d, J=10.3 Hz), 2.01 (1H, br d, J=11.9 Hz), 1.89-1.79 (2H, m), 1.72-1.53 (2H, m), 1.50-1.39 (2H, m) ppm; high resolution mass spectrometry (ES+) m/z 468.2142 [(M+H)$^+$; calculated for C$_{26}$H$_{26}$N$_7$O$_2$: 468.2143].

EXAMPLE 9

(±)-5-[(6'-Methyl-2,3'-bipyridin-5-yl)methyl]-2-(tetrahydro-2H-pyran-3-yl)-2,5-dihydro-3H-pyrazolo[4,3-c]pyrido[3,2-e]pyridazin-3-one

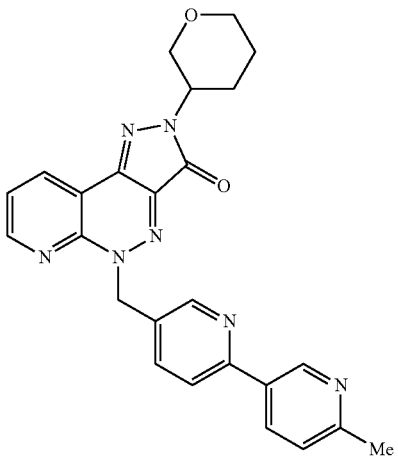

Step 1: Preparation of (±)-tert-butyl 2-(tetrahydro-2H-pyran-3-yl)hydrazinecarboxylate: Dihydro-2H-pyran-3(4H)-one (100 mg, 1.00 mmol), tert-butyl carbazate (145 mg, 1.10 mmol, 1.1 equiv) and acetic acid (0.280 mL, 4.99 mmol, 5 equiv) were combined in 1,2-dichloroethane (3 mL), stirred at ambient temperature for 10 minutes and treated with sodium triacetoxyborohydride (296 mg, 1.34 mmol, 1.4 equiv). After stirring for 1 hour, the mixture was poured into water and extracted with ethyl acetate (3×50 mL). The combined organic extracts were dried with sodium sulfate, filtered and concentrated in vacuo to provide the titled compound.

Step 2: Preparation of (±)-tetrahydro-2H-pyran-3-ylhydrazine hydrochloride: (±)-tert-Butyl 2-(tetrahydro-2H-pyran-3-yl)hydrazinecarboxylate (216 mg, 1.00 mmol) was dissolved in dichloromethane (10 mL) and ethyl acetate (10 mL) and cooled to 0° C. The mixture was saturated with gaseous hydrogen chloride, warmed to ambient temperature and stirred for 1 hour. The mixture was concentrated in vacuo and the residue was concentrated with toluene (2×20 mL) to afford the titled compound.

Step 3: Preparation of (±)-5-[(6'-methyl-2,3'-bipyridin-5-yl)methyl]-2-(tetrahydro-2H-pyran-3-yl)-2,5-dihydro-3H-pyrazolo[4,3-c]pyrido[3,2-e]pyridazin-3-one: Ethyl 1-[(6-methyl-2,3'-bipyridin-5-yl)methyl]-4-thioxo-1,4-dihydropyrido[2,3-c]pyridazine-3-carboxylate [(Example 6, Step 2), 125 mg, 0.299 mmol], (±)-tetrahydro-2H-pyran-3-ylhydrazine hydrochloride (91.0 mg, 0.599 mmol, 2 equiv) and potassium carbonate (414 mg, 2.99 mmol, 10 equiv) were combined in ethanol (10 mL), N,N'-dimethylformamide (3 mL) and dioxane (5 mL) at ambient temperature and after 5 minutes, were warmed to 80° C. for 4 hours. The mixture was cooled to ambient temperature, poured into sodium bicarbonate (100 mL, aqueous saturated) and extracted with ethyl acetate (2×100 mL). The combined organic extracts were dried with sodium sulfate, filtered and concentrated in vacuo. The residue was purified by silica gel gradient chromatography (100:0 to 0:100; hexanes:ethyl acetate containing 10% methanol), providing the titled compound as a deep red solid: $^1$H-NMR (400 MHz, CDCl$_3$) δ 9.02 (1H, d, J=2.1 Hz), 8.93 (1H, d, J=2.3 Hz), 8.75 (1H, dd, J=4.6, 1.8 Hz), 8.51 (1H, dd, J=8.1, 1.8 Hz), 8.16 (1H, dd, J=8.1, 2.4 Hz), 7.97 (1H, dd, J=8.2, 2.3 Hz), 7.66 (1H, dd, J=8.2, 0.6 Hz), 7.50 (1H, dd, J=7.9, 4.6 Hz), 7.24 (1H, d, J=8.1 Hz), 5.97 (1H, br s), 4.70-4.62 (1H, m), 4.01-3.94 (2H, m), 3.74 (1H, ap t, J=10.7 Hz), 3.49 (1H, br m), 3.45 (1H, dd, J=11.1, 3.4 Hz), 2.60 (3H, s), 2.21-2.05 (3H, m) ppm; high resolution mass spectrometry (ES+) m/z 454.1984 [(M+H)$^+$; calculated for C$_{25}$H$_{24}$N$_7$O$_2$: 454.1986].

EXAMPLE 10

(±)-5-{[4-(1H-Pyrazol-1-yl)phenyl]methyl}-2-(tetrahydro-2H-pyran-3-yl)-2,5-dihydro-3H-pyrazolo[4,3-c]pyrido[3,2-e]pyridazin-3-one

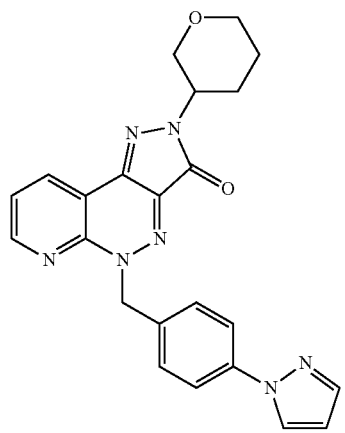

Step 1: Preparation of ethyl 1-[(4-iodophenyl)methyl]-4-oxo-1,4-dihydropyrido[2,3-c]pyridazine-3-carboxylate: Ethyl 4-oxo-1,4-dihydropyrido[2,3-c]pyridazine-3-carboxylate (1.00 g, 4.56 mmol) and 2-chloro-5-(chloromethyl)pyridine [(Example 5, Step 1), 500 mg, 2.28 mmol] and 4-iodobenzylbromide (745 mg, 2.51 mmol, 1.1 equiv) were dissolved in degassed N,N-dimethylformamide (5 mL) and cooled to 0° C. The mixture was treated with sodium hydride (109 mg, 2.74 mmol, 1.2 equiv) portionwise over 5 minutes. After stirring for 2 hours at 0° C., the mixture was warmed to ambient temperature and stirred for an additional 2 hours. The mixture was treated with sodium bicarbonate (10 mL, aqueous saturated), poured into water (50 mL) and extracted with ethyl acetate (2×50 mL). The combined organic extracts were dried with sodium sulfate, filtered, concentrated in vacuo. The residue was purified by silica gel gradient chromatography (100:0 to 0:100; hexanes:ethyl acetate), providing the titled compound.

Step 2: Preparation of ethyl 1-[(4-iodophenyl)methyl]-4-thioxo-1,4-dihydropyrido[2,3-c]pyridazine-3-carboxylate: Ethyl 1-[(4-iodophenyl)methyl]-4-oxo-1,4-dihydropyrido[2,3-c]pyridazine-3-carboxylate (800 mg, 1.84 mmol) was suspended in toluene (5 mL) and dioxane (5 mL) and placed into a preheated oil bath to 110° C. Lawesson's Reagent (409 mg, 1.01 mmol, 0.55 equiv) was added portionwise over 45 minutes and after an additional 30 minutes at 110° C., the mixture was cooled to ambient temperature and concentrated in vacuo. The residue was purified by silica gel gradient chromatography (100:0 to 95:5; dichloromethane:methanol), providing the titled compound.

Step 3: Preparation of (±)-5-[(4-iodophenyl)methyl]-2-(tetrahydro-2H-pyran-3-yl)-2,5-dihydro-3H-pyrazolo[4,3-c]pyrido[3,2-e]pyridazin-3-one: Ethyl 1-[(4-iodophenyl)methyl]-4-thioxo-1,4-dihydropyrido[2,3-c]pyridazine-3-carboxylate (2.0 g, 4.4 mmol), (±)-tetrahydro-2H-pyran-3- ylhydrazine hydrochloride [(Example 9, Step 2), 1.0 g, 6.6 mmol, 1.5 equiv], potassium carbonate (6.1 g, 44 mmol, 10 equiv), and mercury(II) chloride (1.2 g, 4.4 mmol, 1 equiv) were combined in 1,2-dimethoxyethane (20 mL) and N,N-dimethylformamide (4 mL) and stirred at ambient temperature for 1 hour. The mixture was warmed to 50° C. for 20 minutes, treated with additional potassium carbonate (1.0 g, 7.2 mmol, 1.6 equiv) and warmed to 60° C. for 30 minutes. The mixture was heated to 70° C. for 1 hour, cooled to ambient temperature, poured into water (200 mL) and ethyl acetate (200 mL) and filtered through a pad of Celite. The mixture was extracted with ethyl acetate (3×200 mL) and the combined organic extracts were washed with water (50 mL) and brine (50 mL), dried with sodium sulfate, filtered, and concentrated in vacuo. The residue was purified by silica gel gradient chromatography (100:0 to 0:100; hexanes; ethyl acetate), providing the titled compound as a red solid.

Step 4: (±)-5-{[4-(1H-pyrazol-1-yl)phenyl]methyl}-2-(tetrahydro-2H-pyran-3-yl)-2,5-dihydro-3H-pyrazolo[4,3-c]pyrido[3,2-e]pyridazin-3-one: (±)-5-[(4-Iodophenyl)methyl]-2-(tetrahydro-2H-pyran-3-yl)-2,5-dihydro-3H-pyrazolo[4,3-c]pyrido[3,2-e]pyridazin-3-one (50 mg, 0.10 mmol), pyrazole (11 mg, 0.17 mmol, 1.7 equiv), potassium phosphate (71 mg, 0.41 mmol, 4 equiv), (±)-trans-N,N'-dimethylcyclohexane-1,2-diamine (44 mg, 0.31 mmol, 3 equiv) and copper(I) iodide (20 mg, 0.10 mmol, 1 equiv) were combined in degassed N,N-dimethylformamide (2 mL) and placed into a preheated oil bath at 110° C. for 1 hour. The mixture was cooled to ambient temperature, poured into sodium bicarbonate (25 mL, aqueous saturated) and extracted with ethyl acetate (3×50 mL). The combined organic extracts were dried with sodium sulfate, filtered and concentrated in vacuo. The residue was purified by silica gel gradient chromatography (100:0 to 95:5 dichloromethane:methanol), providing the titled compound as a red solid: $^1$H-NMR (400 MHz, CDCl$_3$) δ 8.74 (1H, dd, J=4.5, 1.7 Hz), 8.51 (1H, dd, J=8.0, 1.8 Hz), 8.78 (1H, d, J=2.5 Hz), 7.69 (1H, d, J=1.7 Hz), 7.64-7.62 (4H, m), 7.49 (1H, dd, J=8.0, 4.6 Hz), 6.44 (1H, dd, J=2.5, 1.6 Hz), 5.95 (2H, br s), 4.71-4.63 (1H, m), 4.01-3.95 (2H, m), 3.74 (1H, ap t, J=10.5 Hz), 3.47 (1H, td, J=11.1, 3.6 Hz), 2.22-2.06 (2H, m), 1.92-1.79 (2H, m) ppm; high resolution mass spectrometry (ES+) m/z 428.1837 [(M+H)$^+$; calculated for C$_{23}$H$_{22}$N$_7$O$_2$:428.1829].

EXAMPLE 11

(±)-5-{[4-(6-Methylpyridin-3-yl)phenyl]methyl}-2-(tetrahydro-2H-pyran-3-yl)-2,5-dihydro-3H-pyrazolo[4,3-c]pyrido[3,2-e]pyridazin-3-one

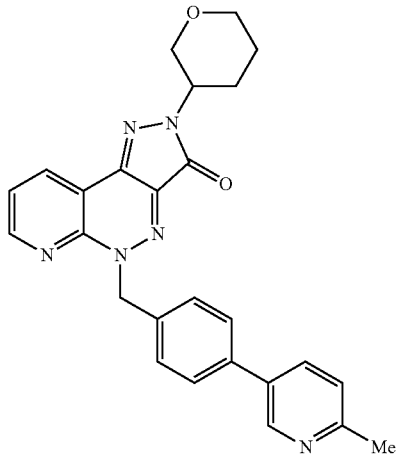

(±)-5-[(4-Iodophenyl)methyl]-2-(tetrahydro-2H-pyran-3-yl)-2,5-dihydro-3H-pyrazolo[4,3-c]pyrido[3,2-e]pyridazin-3-one [(Example 10, Step 3), 50 mg, 0.10 mmol], 2-methyl-5-pyridinylboronic acid (35 mg, 0.26 mmol, 2.5 equiv), palladium(II) acetate (4.6 mg, 0.21 mmol, 0.2 equiv), 1,1'-bis(diphenylphosphino)ferrocene (11 mg, 0.21 mmol, 0.2 equiv), copper(I) chloride (10 mg, 0.10 mmol, 1 equiv) and cesium carbonate (84 mg, 0.26 mmol, 2.5 equiv) were combined in degassed N,N'-dimethylformamide (3 mL) and placed in a preheated oil bath at 100° C. for 1 hour. The mixture was cooled to ambient temperature, poured into sodium bicarbonate (20 mL, aqueous saturated) and extracted with ethyl acetate (3×20 mL). The combined organic extracts were dried with sodium sulfate, filtered, and concentrated in vacuo. The residue was purified via silica gel gradient chromatography (100:0 to 90:10; dichloromethane:methanol), providing the titled compound as a deep red solid: $^1$H-NMR (hydrochloride salt, 400 MHz, CDCl$_3$) δ 8.78 (2H, br s), 8.59 (1H, d, J=6.8 Hz), 8.39 (1H, br s), 7.72 (3H, br s), 7.55 (3H, br s), 6.02 (2H, s), 4.67 (1H, br s), 4.03-3.95 (2H, m), 3.79-3.70 (1H, m), 3.51-3.45 (1H, m), 3.02 (3H, br s), 2.36-2.06 (2H, m), 1.90-1.80 (2H, m) ppm; high resolution mass spectrometry (ES+) m/z 453.2039 [(M+H)$^+$; calculated for C$_{26}$H$_{25}$N$_6$O$_2$: 453.2034].

The following compounds of formula (IIC) were prepared according to the general procedure described in Example 11, substituting the appropriate boronic acid or ester for 2-methyl-5-pyridinylboronic acid, or substituting a suitable catalyst [i.e., bis(tri-tert-butylphosphine)palladium(0)] for palladium(II) acetate and 1,1'-bis(diphenylphosphino)ferrocene. The starting materials are either commercially available, known in the literature or may be prepared from commercially available reagents using conventional reactions well known in the art.

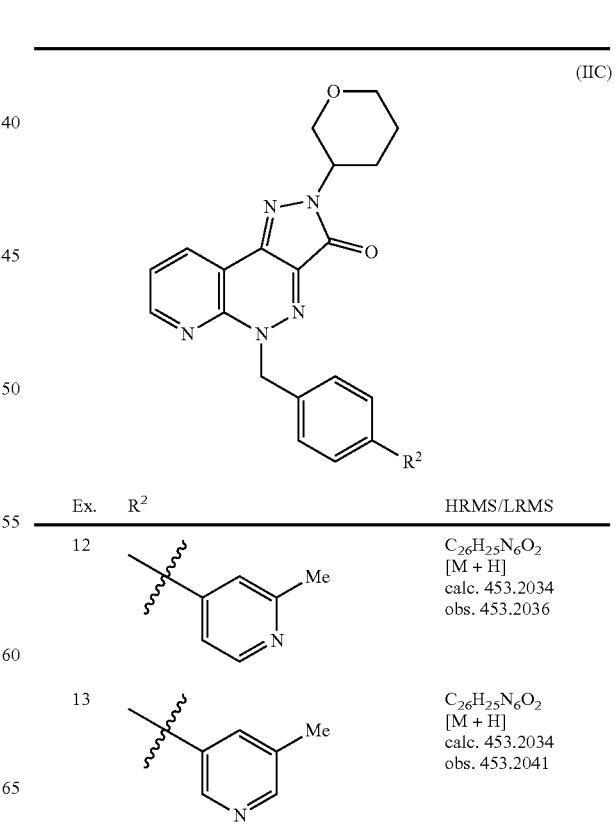

(IIC)

| Ex. | R$^2$ | HRMS/LRMS |
|---|---|---|
| 12 | ![pyridine with Me at 2-position] | C$_{26}$H$_{25}$N$_6$O$_2$ [M + H] calc. 453.2034 obs. 453.2036 |
| 13 | ![pyridine with Me at 3-position] | C$_{26}$H$_{25}$N$_6$O$_2$ [M + H] calc. 453.2034 obs. 453.2041 |

-continued
(IIC)
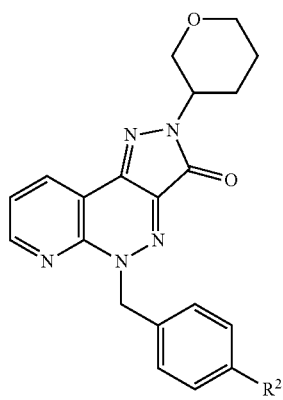
| Ex. | R² | HRMS/LRMS |
|---|---|---|
| 14 | 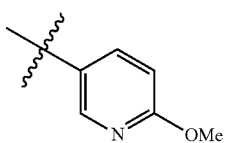 | C₂₆H₂₅N₆O₃ [M + H] calc. 469.1983 obs. 469.1986 |
| 15 | 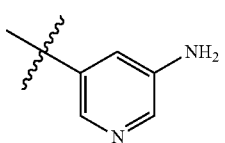 | C₂₅H₂₄N₇O₂ [M + H] calc. 454.1986 obs. 454.1992 |
| 16 | 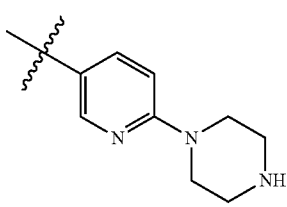 | C₂₉H₃₁N₈O₂ [M + H] calc. 523.2564 obs. 523.2577 |
| 17 | 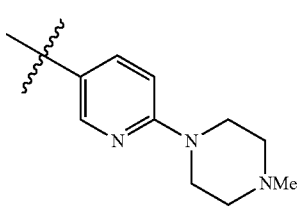 | C₃₀H₃₃N₈O₂ [M + H] calc. 537.2721 obs. 537.2727 |
| 18 | 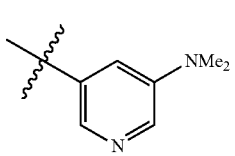 | C₂₇H₂₈N₇O₂ [M + H] calc. 482.2299 obs. 482.2305 |
| 19 | 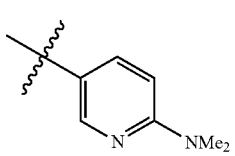 | C₂₇H₂₈N₇O₂ [M + H] calc. 482.2299 obs. 482.2311 |
-continued
(IIC)
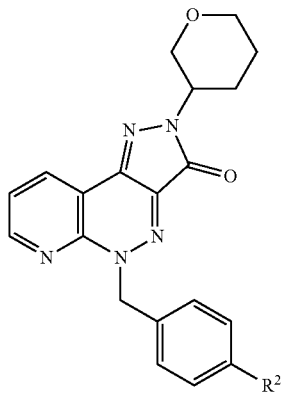
| Ex. | R² | HRMS/LRMS |
|---|---|---|
| 20 | 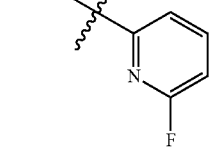 | C₂₅H₂₂FN₆O₂ [M + H] calc. 457.1783 obs. 457.1797 |
| 21 | 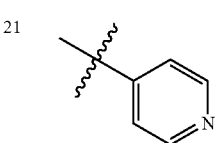 | C₂₅H₂₂FN₆O₂ [M + H] calc. 457.1783 obs. 457.1802 |
| 22 | 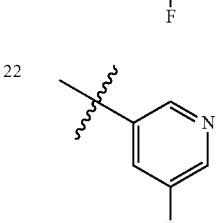 | C₂₅H₂₂FN₆O₂ [M + H] calc. 457.1783 obs. 457.1803 |
| 23 | 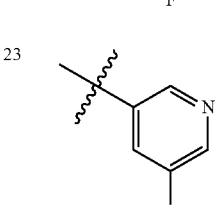 | C₂₆H₂₂N₇O₂ [M + H] calc. 464.1829 obs. 464.1842 |
| 24 | 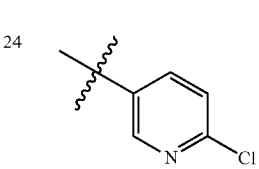 | C₂₅H₂₂ClN₆O₂ [M + H] calc. 473.1487 obs. 473.1498 |
| 25 | 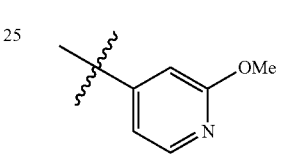 | C₂₆H₂₅N₆O₃ [M + H] calc. 469.1983 obs. 469.1991 |

-continued (IIC)

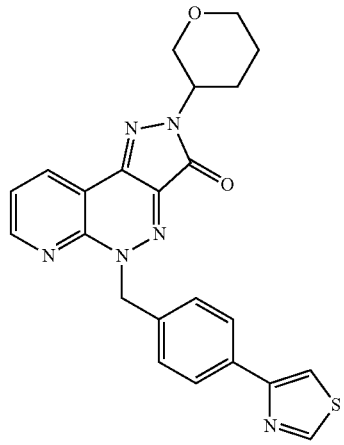

| Ex. | R² | HRMS/LRMS |
|---|---|---|
| 26 | 6-morpholin-4-yl-pyridin-3-yl | C₂₉H₃₀N₇O₃ [M + H] calc. 524.2405 obs. 524.2416 |
| 27 | 5-formyl-pyridin-3-yl (CHO) | C₂₆H₂₃N₆O₃ [M + H] calc. 467.1826 obs. 467.1838 |
| 28 | 5-(methylthio)-pyridin-3-yl (SMe) | C₂₆H₂₅N₆O₂S [M + H] calc. 485.1754 obs. 485.1760 |
| 29 | 5-methoxy-pyridin-3-yl (OMe) | C₂₆H₂₅N₆O₃ [M + H] calc. 469.1983 obs. 469.1988 |
| 30 | 6-fluoro-pyridin-3-yl | C₂₅H₂₂FN₆O₂ [M + H] calc. 457.1783 obs. 457.1784 |

EXAMPLE 31

(±)-2-(Tetrahydro-2H-pyran-3-yl)-5-{[4-(1,3-thiazol-4-yl)phenyl]methyl}-2,5-dihydro-3H-pyrazolo[4,3-c]pyrido[3,2-e]pyridazin-3-one (±)-5-[(4-Iodophenyl)methyl]-2-(tetrahydro-2H-pyran-3-yl)-2,5-dihydro-3H-pyrazolo[4,3-c]pyrido[3,2-e]pyridazin-3-one [(Example 10, Step 3), 40 mg, 0.0.82 mmol], 4-(tributylstannanyl)-1,2-thaiazole (61 mg, 0.16 mmol, 2 equiv), bis(tri-tert-butylphosphine)palladium(0) (42 mg, 0.082 mmol, 1 equiv), copper(I) iodide (7.8 mg, 0.41 mmol, 0.5 equiv) and cesium fluoride (37 mg, 0.25 mmol, 3 equiv) were combined in degassed N,N-dimethylformamide (2 mL) and placed in a preheated oil bath at 80° C. for 45 minutes. The mixture was cooled to ambient temperature, poured into sodium bicarbonate (20 mL, aqueous saturated) and extracted with ethyl acetate (3×20 mL). The combined organic extracts were dried with sodium sulfate, filtered, and concentrated in vacuo. The residue was purified via silica gel gradient chromatography (100:0 to 95: 5; dichloromethane:methanol), providing the titled compound as a deep red solid: ¹H-NMR (hydrochloride salt, 400 MHz, CDCl₃) δ 8.91 (1H, br s), 8.74 (1H, br s), 8.51 (1H, d, J=7.3 Hz), 7.87 (2H, d, J=6.2 Hz), 7.60 (2H, d, J=5.7 Hz), 7.55-7.46 (2H, m), 5.97 (2H, s), 4.71-4.63 (1H, m), 4.03-3.94 (2H, m), 3.75 (1H, ap t, J=11.4 Hz), 3.51-3.43 (1H, m), 2.20-1.80 (4H, m) ppm; high resolution mass spectrometry (ES+) m/z 445.1453 [(M+H)⁺; calculated for C₂₃H₂₁N₆O₂S: 445.1441].

EXAMPLE 32

(±)-5-{[4-(6-Hydroxypyridin-3-yl)phenyl]methyl}-2-(tetrahydro-2H-pyran-3-yl)-2,5-dihydro-3H-pyrazolo[4,3-c]pyrido[3,2-e]pyridazin-3-one

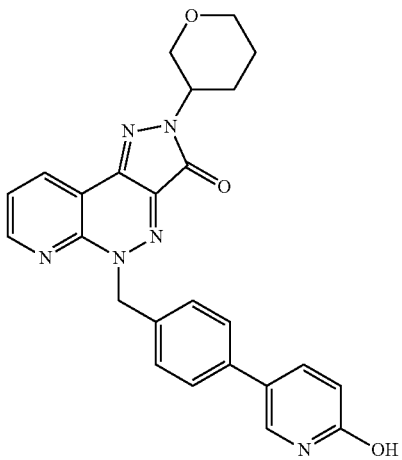

(±)-5-({4-[6-(Methyloxy)pyridin-3-yl]phenyl}methyl)-2-(tetrahydro-2H-pyran-3-yl)-2,5-dihydro-3H-pyrazolo[4,3-c]pyrido[3,2-e]pyridazin-3-one (Example 14, 20 mg, 0.043 mmol) was dissolved in dichloromethane (3 mL), cooled to 0° C. and treated with iodotrimethylsilane (26 µL, 0.13 mmol, 3 equiv). After stirring for 15 minutes at 0° C., the mixture was warmed to ambient temperature and stirred for an additional 14 hours. The mixture was cooled to 0° C. treated with additional iodotrimethylsilane (26 µL, 0.13 mmol, 3 equiv) and after stirring for 15 minutes at 0° C., the mixture was warmed to ambient temperature and stirred for an additional 14 hours. The mixture was treated with methanol (1 mL), poured into water (10 mL) and extracted with ethyl acetate (2×20 mL). The combined organic extracts were dried with sodium sulfate, filtered and concentrated in vacuo. The residue was purified via silica gel gradient chromatography (100:0 to 90:10; dichloromethane:methanol), providing the titled compound as a deep red solid: high resolution mass spectrometry (ES+) m/z 455.1839 [(M+H)+; calculated for $C_{25}H_{23}N_6O_3$: 455.1826].

EXAMPLE 33

2-(2-Methylphenyl)-5-{[4-(1H-pyrazol-1-yl)phenyl]methyl}-2,5-dihydro-3H-pyrazolo[4,3-c]thieno[2,3-e]pyridazin-3-one

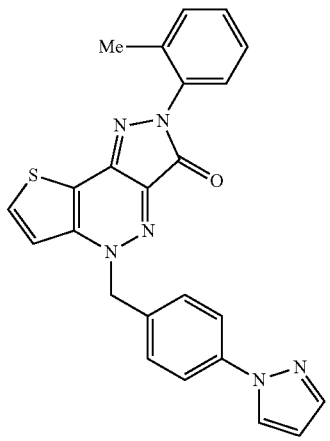

Step 1: Preparation of ethyl 3-(3-chloro-2-thienyl)-3-oxopropanoate: Potassium 3-(ethyoxy)-3-oxopropanoate (1.97 g, 11.6 mmol, 2.1 equiv) was suspended in acetonitrile (15 mL), cooled to 0° C. and treated with successively with triethylamine (2.46 mL, 17.7 mmol, 3.2 equiv) and magnesium (II) chloride (1.31 g, 13.8 mmol, 2.5 equiv). The ice bath was removed and the mixture was warmed to ambient temperature and stirred for an additional for 2.5 hours. An acetonitrile solution (5 mL) of 3-chlorothiophene-2-carbonyl chloride (1.00 g, 5.52 mmol) was added and the mixture was stirred for 72 hours at ambient temperature. The mixture was concentrated in vacuo and the residue was concentrated from toluene (1×75 mL), providing a white solid. The solid was suspended in toluene (~50 mL), cooled to 0° C. and treated with hydrochloric acid (~20 mL, 12 N aqueous) with vigorous stirring. After 15 minutes, the ice bath was removed and the mixture was warmed to ambient temperature and stirred for 45 minutes. The mixture was poured into water (50 mL) and extracted with ethyl acetate (3×75 mL). The combined organic extracts were dried with sodium sulfate, filtered and concentrated in vacuo. The residue was purified by silica gel gradient chromatography (100:0 to 75:25; hexanes:ethyl acetate), providing the titled compound.

Step 2: Preparation of ethyl 3-(3-chloro-2-thienyl)-2-diazo-3-oxopropanoate: Ethyl 3-(3-chloro-2-thienyl)-3-oxopropanoate (1.26 g, 5.42 mmol) was dissolved in anhydrous acetonitrile (10 mL), treated with triethylamine (0.63 mL, 6.2 mmol, 1.15 equiv) and cooled to 0° C. To the mixture was added 4-acetamidobenzenesulfonyl azide (1.43 g, 6.0 mmol, 1.1 equiv) and after 10 minutes at 0° C., the mixture was warmed to ambient temperature. To the mixture, additional acetonitrile (20 mL) was added and the mixture was stirred at ambient temperature for an additional 45 minutes. The mixture was treated with sodium hydroxide (10 mL, 1 N aqueous), sodium carbonate (25 mL, aqueous saturated) and water (75 mL) and then extracted with ethyl acetate (2×150 mL). The combined organic extracts were dried with sodium sulfate, filtered and concentrated in vacuo. The residue was purified by silica gel gradient chromatography (100:0 to 70:30; hexanes:ethyl acetate), providing the titled compound.

Step 3: Preparation of ethyl(2Z)-3-(3-chloro-2-thienyl)-2-hydrazono-3-oxopropanoate: Ethyl 3-(3-chloro-2-thienyl)-2-diazo-3-oxopropanoate (662 mg, 2.56 mmol) was dissolved in dioxane (10 mL), treated with tri-n-butylphosphine (0.663 mL, 2.69 mmol, 1.05 equiv) and stirred at ambient temperature for 30 minutes. The mixture was poured into sodium bicarbonate (100 mL, aqueous saturated) and extracted with ethyl acetate (3×100 mL). The combined organic extracts were dried with sodium sulfate, filtered and concentrated in vacuo. The residue was purified by silica gel gradient chromatography (100:0 to 1:1; hexanes:ethyl acetate), providing the titled compound.

Step 4: Preparation of ethyl (2Z)-3-(3-chloro-2-thienyl)-3-oxo-2-9{[4-(1H-pyrazol-1-yl)phenyl]methyl}hydrazono) propanoate: Ethyl (2Z)-3-(3-chloro-2-thienyl)-2-hydrazono-3-oxopropanoate (484 mg, 1.86 mmol) and 1-[4-(bromomethyl)phenyl]-1H-pyrazole (484 mg, 2.04 mmol, 1.1 equiv) were dissolved in degassed N,N-dimethylformamide (8 mL) and cooled to 0° C. Sodium hydride (120 mg, 3.00 mmol, 1.62 equiv, 60% dispersion in mineral oil) was added in one portion and the mixture was stirred for 30 minutes at 0° C. The mixture was treated with ammonium chloride (1 mL, aqueous saturated), warmed to ambient temperature, poured into sodium bicarbonate (50 mL, aqueous saturated) and extracted with ethyl acetate (3×100 mL). The combined organic extracts were dried with sodium sulfate, filtered and concentrated in vacuo. The residue was purified by silica gel gradient chromatography (100:0 to 25:75; hexanes:ethyl acetate), providing the titled compound.

Step 5: Preparation of ethyl 4-oxo-1-{[4-(1H-pyrazol-1-yl)phenyl]methyl}-1,4-dihydrothieno[3,2-c]pyridazine-3-carboxylate: Ethyl(2Z)-3-(3-chloro-2-thienyl)-3-oxo-2-9{[4-(1H-pyrazolo-1-yl)phenyl]methyl}hydrazono) propanoate (347 mg, 0.823 mmol) was dissolved in degassed N,N-dimethylformamide (5 mL), treated with potassium carbonate (230 mg, 1.66 mmol, 2 equiv) and placed into an oil bath preheated at 120° C. for 30 minutes. The mixture was cooled to ambient temperature, poured into sodium bicarbonate (75 mL, aqueous saturated) and extracted with ethyl acetate (3×50 mL). The combined organic extracts were dried with sodium sulfate, filtered and concentrated in vacuo. The residue was purified by silica gel gradient chromatography (100:0 to 0:100; hexanes:ethyl acetate), providing the titled compound as a light yellow oil.

Step 6: Preparation of ethyl 4-thioxo-1-{[4-(1H-pyrazol-1-yl)phenyl]methyl}-1,4-dihydrothieno[3,2-c]pyridazine-3-carboxylate: Ethyl 4-oxo-1-{[4-(1H-pyrazol-1-yl)phenyl]methyl}-1,4-dihydrothieno[3,2-c]pyridazine-3-carboxylate (37 mg, 0.097 mmol) suspended in dioxane (5 mL) and toluene (5 mL), placed into an oil bath preheated at 110° C. and treated with Lawesson's Reagent (39 mg, 0.097 mmol, 1 equiv) portionwise over 10 minutes. The mixture was heated for an additional 30 minutes, cooled to ambient temperature and concentrated in vacuo. The residue was purified by silica gel gradient chromatography (100:0 to 25:75; hexanes:ethyl acetate), providing the titled compound as a brown oil.

Step 7: Preparation of 5-{[4-(1H-pyrazol-1-yl)phenyl]methyl}-2,5-dihydro-3H-pyrazol[4,3-c]thieno[2,3-e]pyridazin-3-one: Ethyl 4-thioxo-1-{[4-(1H-pyrazol-1-yl)phenyl]methyl}-1,4-dihydrothieno[3,2-c]pyridazine-3-carboxylate (23 mg, 0.058 mmol) and hydrazine (1.0 mL, 31 mmol, 550 equiv) were combined in absolute ethanol (7 mL) and placed into an oil bath preheated to 85° C. for 2 hours. The mixture was cooled to ambient temperature and concentrated in vacuo, providing the titled compound.

Step 8: Preparation of 2-(2-methylphenyl)-5-{[4-(1H-pyrazol-1-yl)phenyl]methyl}-2,5-dihydro-3H-pyrazolo[4,3-c]thieno[2,3-e]pyridazin-3-one: 5-{[4-(1H-Pyrazol-1-yl)phenyl]methyl}-2,5-dihydro-3H-pyrazol[4,3-c]thieno[2,3-e]pyridazin-3-one (20 mg, 0.058 mmol), 2-iodotoluene (38 mg, 0.17 mmol, 3 equiv), copper(I) iodide (11 mg, 0.058 mmol, 1 equiv), (±)-trans-N,N'-dimethylcyclohexane-1,2-diamine (24 mg, 0.17 mmol, 3 equiv) and potassium phosphate (86 mg, 0.41 mmol, 7 equiv) were combined in degassed N,N-dimethylformamide (3 mL) and placed into an oil bath preheated to 110° C. for 2 hours. The mixture was cooled to ambient temperature, poured into sodium bicarbonate (25 mL, aqueous saturated) and extracted with ethyl acetate (2×75 mL). The combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound as a deep red solid: $^1$H-NMR (400 MHz, CDCl$_3$) δ 7.91 (1H, d, J=2.5 Hz), 7.73-7.71 (3H, m), 7.66 (1H, d, J=5.6 Hz), 7.46-7.43 (3H, m), 7.36-7.27 (4H, m), 6.47 (1H, dd, J=2.4, 1.9 Hz), 5.83 (2H, s), 2.35 (3H, s) ppm; high resolution mass spectrometry (ES+) m/z 439.1336 [(M+H)$^+$; calculated for C$_{24}$H$_{19}$N$_6$OS: 439.1336].

The following compounds of formula (IIIA) were prepared according to the general procedure described in Example 33, substituting the appropriate iodide for 2-iodotoluene (Step 8). The starting materials are either commercially available, known in the literature or may be prepared from commercially available reagents using conventional reactions well known in the art.

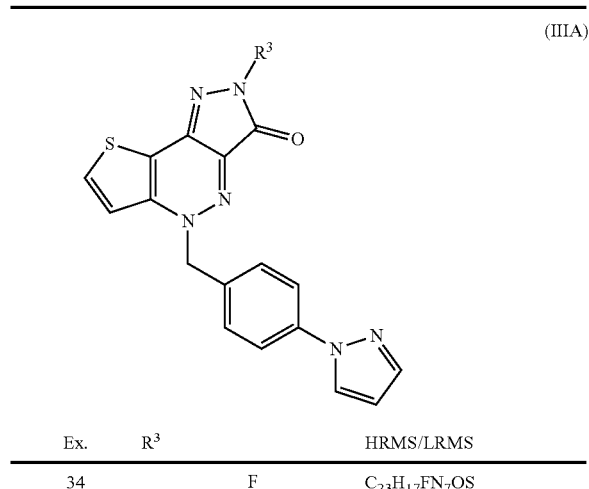

(IIIA)

| Ex. | R$^3$ | HRMS/LRMS |
|---|---|---|
| 34 | Me, F pyridyl | C$_{23}$H$_{17}$FN$_7$OS [M + H] calc. 458.1194 obs. 458.1210 |

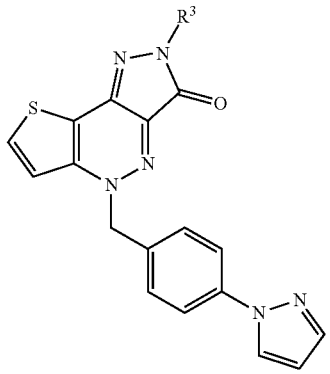

(IIIA)

| Ex. | R$^3$ | HRMS/LRMS |
|---|---|---|
| 35 | F-phenyl | C$_{23}$H$_{16}$FN$_6$OS [M + H] calc. 443.1085 obs. 443.1077 |
| 36 | 2,3-Me$_2$-phenyl | C$_{25}$H$_{21}$N$_6$OS [M + H] calc. 453.1492 obs. 453.1483 |

EXAMPLE 37

(±)-5-{[4-(1H-Pyrazol-1-yl)phenyl]methyl}-2-(tetrahydro-2H-pyran-3-yl)-2,5-dihydro-3H-pyrazolo[4,3-c]thieno[2,3-e]pyridazin-3-one

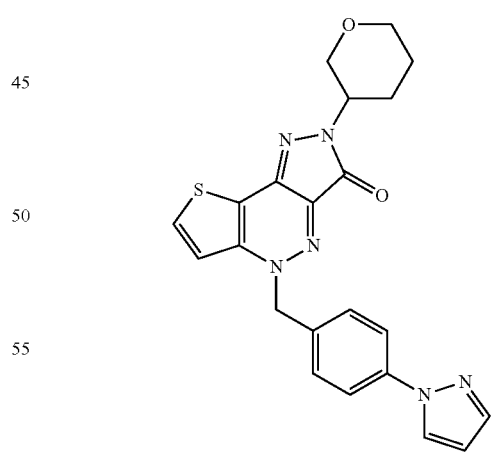

Ethyl 4-thioxo-1-{[4-(1H-pyrazol-1-yl)phenyl]methyl}-1,4-dihydrothieno[3,2-c]pyridazine-3-carboxylate [(Example 33, Step 6), 134 mg, 0.338 mmol] was dissolved in dioxane (4 mL) and treated with dry meta-chloroperoxybenzoic acid (58 mg, 0.338 mmol, 1 equiv), providing an activated thioketone solution. In a separate flask, (±)-tetrahydro-2H-pyran-3-ylhydrazine hydrochloride [(Example 9, Step 2), 214 mg, 1.4 mmol, 4.14 equiv] was suspended in N,N-dimethylformamide (7 mL) and treated with N,N-diiospropylethylamine (0.472 mL, 2.7 mmol, 8 equiv). To this mixture was added the activated thioketone solution followed by potassium carbonate (467 mg, 3.38 mmol, 10 equiv). After stirring vigorously for 30 minutes, the mixture was heated to 120° C. for 4 hours. The mixture was cooled to ambient temperature, poured into sodium bicarbonate (100 mL) and extracted with ethyl acetate (2×100 mL). The combined organic extracts were dried with sodium sulfate, filtered and concentrated in vacuo. The residue was purified by silica gel gradient chromatography (100:0 to 0:100; hexanes:ethyl acetate containing 10% methanol), providing the titled compound as a reddish brown solid: $^1$H-NMR (400 MHz, CDCl$_3$) δ 7.89 (1H, d, J=2.4 Hz), 7.71 (1H, d, J=1.6 Hz), 7.68 (2H, d, J=8.7 Hz), 7.63 (1H, d, J=5.6 Hz), 7.38 (2H, d, J=8.6 Hz), 7.23 (1H, d, J=5.6 Hz), 6.46 (1H, dd, J=2.4, 1.9 Hz), 5.79 (2H, s), 4.78-4.70 (1H, m), 4.03 (1H, ddd, J=10.6, 4.5, 1.7 Hz), 3.97 (1H, br d, J=10.9 Hz), 3.80 (1H, ap t, J=10.6 Hz), 3.49 (1H, td, J=11.1, 3.1 Hz), 2.22 (1H, ddd, J=17.1, 12.2, 5.1 Hz), 2.10 (1H, br d, J=12.0 Hz), 1.94-1.79 (2H, m) ppm; high resolution mass spectrometry (ES+) m/z 433.1440 [(M+H)$^+$; calculated for C$_{22}$H$_{21}$N$_6$O$_2$S: 433.1441].

EXAMPLE 38

(±)-5-{[4-(6-Methylpyridin-3-yl)phenyl]methyl}-2-(tetrahydro-2H-pyran-3-yl)-2,5-dihydro-3H-pyrazolo[4,3-c]thieno[2,3-e]pyridazin-3-one

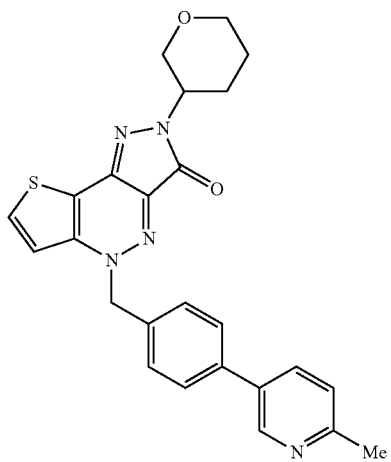

Step 1: Preparation of ethyl(2Z)-3-(3-fluoro-2-thienyl)-2-hydrazone-3-oxopropanoate: Using the procedures described in Example 33, substituting 3-fluorothiophene-2-carbonyl chloride (derived from the known 3-fluorothiophene-2-carboxylic acid) for 3-chlorothiophene-2-carbonyl chloride (Step 1), the titled compound was obtained.

Step 2: Preparation of ethyl [(4-iodophenyl)methyl]-4-oxo-1,4-dihydrothieno[3,2-c]pyridazine-3-carboxylate: Ethyl(2Z)-3-(3-fluoro-2-thienyl)-2-hydrazono-3-oxopropanoate (5.73 g, 23.5 mmol) and 4-iodobenzylbromide (7.31 g, 24.6 mmol, 1.05 equiv) were dissolved in degassed N,N-dimethylformamide (47 mL) and cooled to 0° C. Sodium hydride (1.03 g, 25.8 mmol, 1.1 equiv, 60% dispersion in mineral oil) was added portionwise over 30 minutes and was stirred for an additional 2 hours at 0° C. Additional sodium hydride (1.03 g, 25.8 mmol, 1.1 equiv, 60% dispersion in mineral oil) was added and the mixture was stirred at 0° C. for an additional 1 hour. The mixture was carefully treated with sodium bicarbonate (5 mL, aqueous saturated) and then poured into sodium bicarbonate (200 mL, aqueous saturated) and water (250 mL). The aqueous layer was treated with ethyl acetate (400 mL), upon which a thick precipitate formed. The mixture was filtered and the solid was collected and dried in vacuo, providing the titled compound. The filtrate (organic and aqueous) was extracted with ethyl acetate (2×400 mL) and the combined organic extracts were washed with brine (50 mL), dried with sodium sulfate, filtered and concentrated in vacuo. The residue was purified by silica gel gradient chromatography (100:0 to 1:100; hexanes:ethyl acetate), providing additional titled compound.

Step 3: Preparation of ethyl[(4-iodophenyl)methyl]-4-thioxo-1,4-dihydrothieno[3,2-c]pyridazine-3-carboxylate: Ethyl[(4-iodophenyemethyl]-4-oxo-1,4-dihydrothieno[3,2-c]pyridazine-3-carboxylate (410 mg, 0.931 mmol) was suspended in toluene (10 mL) and dioxane (10 mL) and placed into an oil bath preheated at 100° C. Lawesson's Reagent (207 mg, 0.512 mmol, 0.55 equiv) was added portionwise over 10 minutes and the mixture was heated for an additional 30 minutes at 100° C., cooled to ambient temperature and concentrated in vacuo. The residue was purified by silica gel gradient chromatography (100:0 to 50:50; hexanes:ethyl acetate), providing the titled compound as a reddish brown solid.

Step 4: Preparation of (±)-5-[(4-iodophenyl)methyl]-2-(tetrahydro-2H-pyran-3-yl)-2,5-dihydro-3H-pyrazolo[4,3-c]thieno[2,3-e]pyridazin-3-one: Ethyl[(4-iodophenyl)methyl]-4-thioxo-1,4-dihydrothieno[3,2-c]pyridazine-3-carboxylate (523 mg, 1.15 mmol) was dissolved in dioxane (10 mL) and treated with dry meta-chloroperoxybenzoic acid (198 mg, 1.15 mmol, 1 equiv), providing an activated thioketone solution. In a separate flask, (±)-tetrahydro-2H-pyran-3-ylhydrazine hydrochloride [(Example 9, Step 2), 525 mg, 3.44 mmol, 3 equiv] was suspended in N,N-dimethylformamide (20 mL) and treated with diisopropylethylamine (1.00 mL, 5.73 mmol, 5 equiv). To this mixture was added the activated thioketone solution followed by potassium carbonate (1.58 g, 11.5 mmol, 10 equiv). After stirring vigorously for 30 minutes, the mixture was heated to 120° C. for 4 hours. The mixture was cooled to ambient temperature, poured into sodium bicarbonate (100 mL) and extracted with ethyl acetate (2×100 mL). The combined organic extracts were dried with sodium sulfate, filtered and concentrated in vacuo. The residue was purified by silica gel gradient chromatography (100:0 to 0:100; hexanes:ethyl acetate containing 10% methanol), providing the titled compound as a reddish brown solid.

Step 5: Preparation of (±)-5-{[4-(6-methylpyridin-3-yl)phenyl]methyl}-2-(tetrahydro-2H-pyran-3-yl)-2,5-dihydro-3H-pyrazolo[4,3-c]thieno[2,3-e]pyridazin-3-one: (±)-5-[(4-Iodophenyl)methyl]-2-(tetrahydro-2H-pyran-3-yl)-2,5-dihydro-3H-pyrazolo[4,3-c]thieno[2,3-e]pyridazin-3-one (50 mg, 0.10 mmol), cesium carbonate (66 mg, 0.20 mmol, 2 equiv), copper(I) chloride (10 mg, 0.10 mmol, 1 equiv), 2-methyl-5-pyridinylboronic acid (22 mg, 0.14 mmol, 1.4 equiv), palladium(II) acetate (2.3 mg, 10 µmol, 0.1 equiv), and 1,1'-bis(diphenylphosphino)ferrocene (11 mg, 20 µmol, 0.2 equiv) were combined in N,N-dimethylformamide (3 mL) and placed into a preheated oil bath at 90° C. for 30 minutes. The mixture was cooled to ambient temperature, poured into water (20 mL) and extracted with ethyl acetate (3×75 mL). The combined organic extracts were washed with water (50 mL) and brine (50 mL), dried with sodium sulfate, filtered and concentrated in vacuo. The residue was purified by silica gel gradient chromatography (100:0 to 0:100; hexnaes:ethyl acetate containing 10% methanol), providing the titled compound: $^1$H-NMR (400 MHz, CDCl$_3$) δ 8.70 (1H, br s), 7.77 (1H, d, J=8.2 Hz), 7.65 (1H, d, J=5.6 Hz), 7.54 (2H, d, J=8.3 Hz), 7.39 (2H, d, J=8.3 Hz), 7.27-7.24 (2H, in), 5.81 (2H, s), 4.78-4.70 (1H, m), 4.02 (1H, dd, J=10.8, 3.9 Hz), 3.97 (1H, br d, J=11.4 Hz), 3.80 (1H, ap t, J=10.5 Hz), 3.49 (1H, td, J=11.3, 3.1 Hz), 2.62 (3H, s), 2.22 (1H, ddd, J=17.2, 12.3, 5.0 Hz), 2.10 (1H, br d, J=11.3 Hz), 1.94-1.80 (2H, m) ppm; high resolution mass spectrometry (ES+) m/z 458.1642 [(M+H)$^+$; calculated for C$_{25}$H$_{24}$N$_5$O$_2$S: 458.1645].

EXAMPLE 39

(±)-5-{[4-(2-Methylpyridin-4-yl)phenyl]methyl}-2-(tetrahydro-2H-pyran-3-yl)-2,5-dihydro-3H-pyrazolo[4,3-c]thieno[2,3-e]pyridazin-3-one

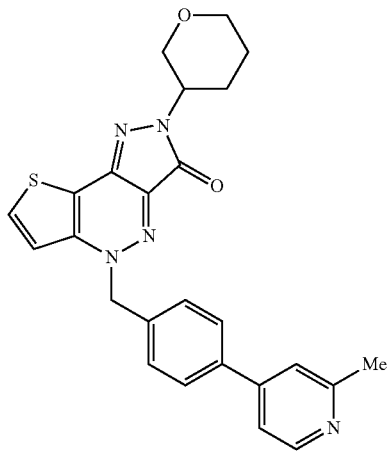

Using the procedures described in Example 38, substituting 2-methyl-4-pyridinylboronic acid for 2-methyl-5-pyridinylboronic acid (Step 5), the titled compound was obtained: $^1$H-NMR (400 MHz, CDCl$_3$) δ 8.56 (1H, br s), 7.64 (1H, d, J=5.6 Hz), 7.60 (2H, d, J=8.3 Hz), 7.40 (2H, d, J=8.3 Hz), 7.35 (1H, br m), 7.30 (1H, br m), 7.24 (1H, d, J=5.8 Hz), 5.82 (2H, s), 4.78-4.70 (1H, m), 4.03 (1H, dd, J=10.6, 1.4 Hz), 3.97 (1H, br d, J=11.8 Hz), 3.80 (1H, ap t, J=10.6 Hz), 3.49 (1H, td, J=11.4, 3.1 Hz), 2.64 (3H, s), 2.22 (1H, ddd, J=17.3, 12.1, 5.5 Hz), 2.14-2.07 (1H, m), 1.94-1.79 (2H, m) ppm; high resolution mass spectrometry (ES+) m/z 458.1640 [(M+H)$^+$; calculated for C$_{25}$H$_{24}$N$_5$O$_2$S: 458.1645].

Biological Utility

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a FLIPR$^{384}$ Fluorometric Imaging Plate Reader System. The assay studies the effect of one or several concentrations of test compounds on basal or acetylcholine-stimulated Ca$^{2+}$ levels using FLIPR.

Compounds are prepared and subjected to a preincubation period of 4 min. Thereafter, a single EC$_{20}$ concentration of acetylcholine is added to each well (3 nM final). The intracellular Ca$^{2+}$ level of each sample is measured and compared to an acetylcholine control to determine any modulatory activity Cells: CHOnfat/hM1, hM2, hM3 or hM4 cells are plated 24 hr before the assay at a density of 18,000 cells/well (100 µL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 120 µL addition plate; 96-well Whatman 2 ml Uniplate Incubator, 37° C., 5% CO$_2$; Skatron EMBLA-384 Plate Washer; Multimek Pipetting System; Genesis Freedom 200 System; Mosquito System; Temo Nanolitre Pipetting System; and FLIPR$^{384}$ Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 µM in buffer for a final concentration of 1 µM in Assay. 20% Pluronic Acid Solution stock, with concentration of 0.04% in Buffer, 0.02% in Assay.

65 µL of 2 mM Fluo-4AM are mixed with 130 µL of 20% Pluronic Acid. The resulting solution and 650 µL FBS is added to the assay buffer for a total volume of 65 mL. Positive Controls; 4-Br-A23187: 10 mM in DMSO; final concentration 10 µM. Acetylcholine: 10 mM in water, working stock at both 20 µM and 30 µM in assay buffer, final concentration of 10 µM. This is used to check the maximum stimulation of the CHOK1/hM1 cells. 20 µM (2×) acetylcholine is added in the preincubation part of the assay, and the 30 µM (3×) stock is added in the second part. (EC$_{20}$)Acetylcholine; 10 mM in water, working stock of 9 nM (3×), and final concentration in assay is 3 nM. This is used after the preincubation with test compounds. Addition of the EC$_{20}$ Acetylcholine to each well with a test compound will ascertain any modulator activity. 24 wells contain 3 nM Acetylcholine alone as a control.

Determining Activity of Putative Compounds:

Screening Plate: Compounds are titrated in 96-well plates (columns 2-11), 100% DMSO, started at a concentration of 15 mM (150× stock concentration), and 3-fold serial dilutions using Genesis Freedom 200 System. Four 96-well plates are combined into a 384-well plate using Mosquito Nanolitre Pipetting System by transferring 1 µl of serial diluted compounds to each well, and 1 mM acetylcholine (100× stock concentration) were added as a control. Using Temo, 49 µl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 µM acetylcholine control (3×) is added into control wells, and the 3× agonist plate is transferred into a 384 well plate.

Cells are washed three times with 100 µL of buffer, leaving 30 µL of buffer in each well. Using Multimek, 30 µL of Dye Loading Buffer is added into each well and incubated at 37° C., 5% CO$_2$ for up to one hr.

After 60 min, the cells are washed three times with 100 µL of buffer, leaving 30 µL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the $EC_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 μM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 1 below:

| Example | IP Value (nM) |
|---------|---------------|
| 1 | 58 |
| 4 | 366 |
| 5 | 109 |
| 6 | 36 |
| 8 | 140 |
| 9 | 1159 |
| 10 | 438 |
| 11 | 370 |
| 13 | 578 |
| 31 | 295 |
| 32 | 1691 |
| 33 | 48 |
| 34 | 33 |
| 37 | 96 |
| 38 | 183 |
| 39 | 120 |

The following abbreviations are used throughout the text:

| | |
|---|---|
| Me: | methyl |
| Et: | ethyl |
| Bu: | butyl |
| t-Bu: | tert-butyl |
| Ar: | aryl |
| Ph: | phenyl |
| Bn: | benzyl |
| DMF: | dimethylformamide |
| Ac: | acetyl |
| DMSO: | dimethylsulfoxide |
| DMEM: | Dulbecco's Modified Eagle Medium (High Glucose) |
| FBS: | fetal bovine serum |
| rt: | room temperature |
| aq: | aqueous |
| HPLC: | high performance liquid chromatography |
| MS: | mass spectrometry |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

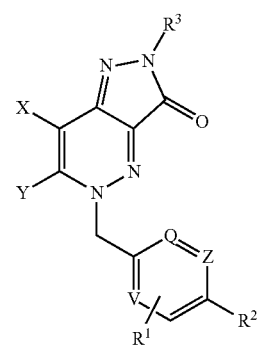

and pharmaceutically acceptable salts thereof, wherein

Q, V and Z are each selected from the group consisting of
1) —CH, and
2) N;

X and Y are linked together to form a fused ring moiety selected from the group consisting of

1)

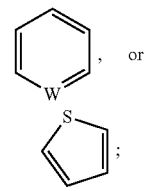

, or (2)

W is selected from the group consisting of
1) —CH, and
2) —N;

$R^1$ is optionally present at one or more of the ring carbon atoms, and is selected from the group consisting of
(1) —$C_{1-6}$ alkyl,
(2) —O—$C_{1-6}$ alkyl, or
(3) halogen;

$R^2$ is selected from the group consisting of
(1) aryl,
(2) a heteroaryl group which is an aromatic cyclic group, having from five to twelve ring atoms, said ring atoms selected from C, O, N or S, at least one of which is O, N or S,
(3) halogen,
wherein said aryl or heteroaryl is optionally substituted with one or more
(a) halogen,
(b) hydroxy,
(c) —O—$C_{1-6}$ alkyl,
(d) —$C_{1-6}$ alkyl,
(e) cyano, (f) —NR^A R^B, wherein R^A and R^B are selected from the group consisting of
  (i) hydrogen, or
  (ii) —C_{1-6} alkyl,
  or R^A and R^B are linked together with the nitrogen to which they are both attached to form a 2-6 membered carbocyclic ring, wherein one or two of the ring carbon atoms is replaced by a nitrogen, oxygen or sulfur, and the carbocyclic is optionally substituted with one or more C_{1-6} alkyl,
(g) —C(=O)—R^C, wherein R^C is selected from the group consisting of
  (i) hydrogen, or
  (ii) —C_{1-6} alkyl, or
(h) —S(O)_n—R^C;
R^3 is selected from the group consisting of
  (1) aryl,
  (2) a heteroaryl group, which is an aromatic cyclic group, having from five to twelve ring atoms, said ring atoms selected from C, O, N or S, at least one of which is O, N or S,
  (3) —C_{5-10} cycloalkyl, or
  (4) a heterocyclic group, which is a nonaromatic cyclic group, having from five to twelve ring atoms, said ring atoms selected from C, O, N or S, at least one of which is O, N or S,
  wherein said aryl, heteroaryl cycloalkyl or heterocyclic group is optionally substituted with one or more
  (a) halogen,
  (b) hydroxy,
  (c) —O—C_{1-6} alkyl, or
  (d) —C_{1-6} alkyl;
n is 0, 1 or 2.

2. A compound of claim 1, wherein X and Y are linked together to form the fused ring moiety:

3. A compound of claim 1, wherein X and Y are linked together to form the fused ring moiety:

4. A compound of 2, wherein V, Q and Z are CH.

5. A compound of claim 2, wherein V and Q are CH, and Z is N.

6. A compound of claim 1, wherein R^2 is heteroaryl.

7. A compound of claim 1, wherein R^2 is aryl.

8. A compound of claim 1, wherein R^3 is aryl.

9. A compound of claim 1, wherein R^3 is heteroaryl.

10. A compound of claim 1, wherein R^3 is cycloalkyl.

11. A compound of claim 1, wherein R^3 is heterocyclic.

12. A compound of claim 1, wherein the compound of formula (I) is a compound of formula (II):

(II)

and pharmaceutically acceptable salts thereof, wherein V, Q, Z, R^1, R^2 and R^3 are as previously defined.

13. A compound of claim 12, wherein the compound of formula (II) is a compound of formula (IIA)

(IIA)

wherein R^2 is selected from the group consisting of or a pharmaceutically acceptable salt thereof.

14. A compound of claim 12, wherein the compound of formula (II) is a compound of formula (IIB)
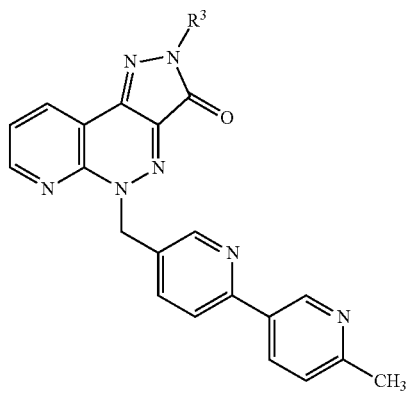
(IIB)
wherein R³ is selected from the group consisting of
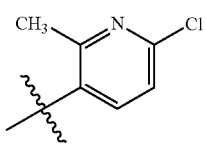
or a pharmaceutically acceptable salt thereof.
15. A compound of claim 12, wherein the compound of formula (II) is a compound of formula (IIC)
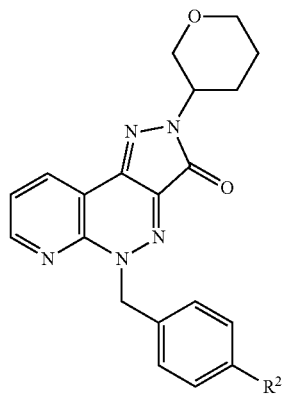
(IIC)
wherein R² is selected from the group consisting of
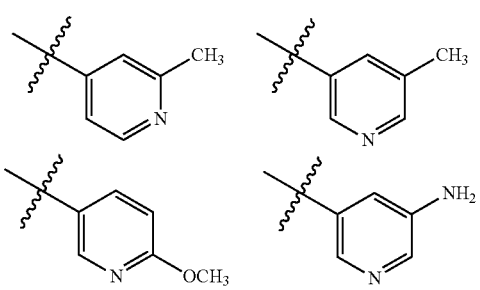
-continued
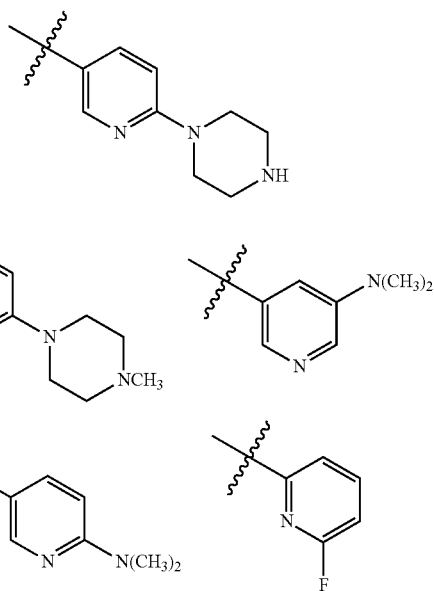
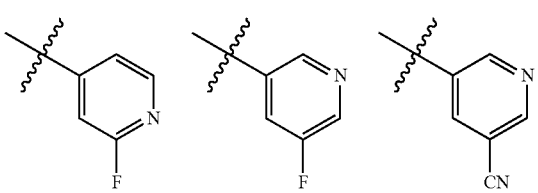
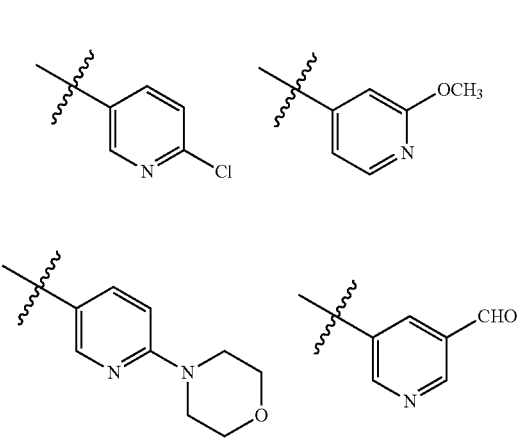
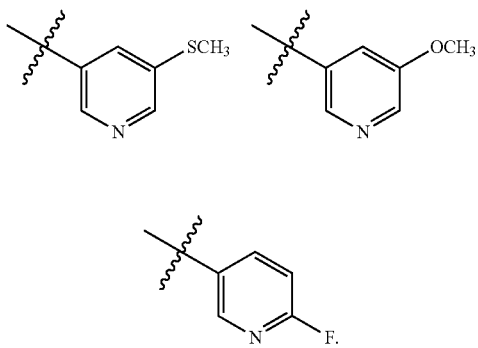

16. A compound of claim 1, wherein the compound of formula (I) is a compound of formula (III):

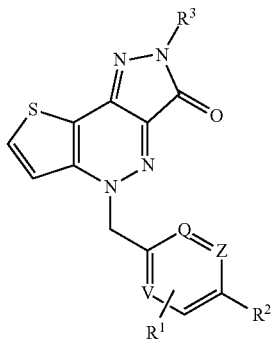

(III)

and pharmaceutically acceptable salts thereof, wherein V, Q, Z, $R^1$, $R^2$ and $R^3$ are defined in claim 1.

17. A compound of claim 16, wherein the compound of formula (III) is a compound of formula (IIIA)

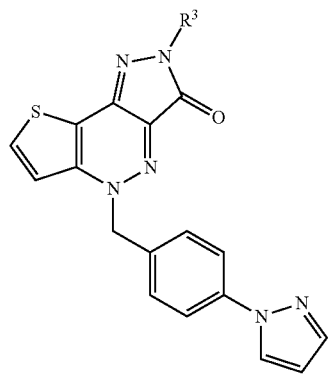

(IIIA)

wherein $R^3$ is selected from the group consisting of

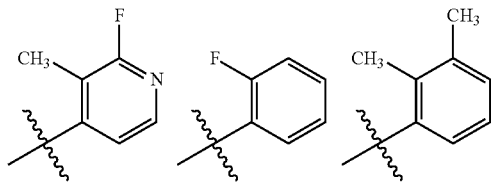

or a pharmaceutically acceptable salt thereof.

18. A compound which is selected from the group consisting of 2-(2,3-Dimethylphenyl)-5 -{[6-(1-methyl-1H-pyrazol-4-yl)pyridin-3-yl]methyl} -2,5-dihydro -3H-pyrazolo[4,3-c]pyrido[3,2-e]pyridazin-3-one;

5-[(6-Chloropyridin-3-yl)methyl]-2-(2,3-dimethylphenyl)-2,5-dihydro-3H-pyrazolo[4,3-c ]pyrido[3,2-e]pyridazin-3-one;

2-(2,3-Dimethylphenyl)-5-[(6'-methyl-2,3'-bipyridin-5-yl)methyl]-2,5-dihydro-3H-pyrazolo [4,3-c]pyrido[3,2-e]pyridazin-3-one;

2-(2-Fluoro-3-methylphenyl)-5-[(6'-methyl-2,3'-bipyridin-5-yl)methyl]-2,5-dihydro-3H-pyrazolo [4,3-c]pyrido[3,2-e]pyridazin-3-one;

(±)-2-(trans-2-Hydroxycyclohexyl)-5-[(6'-methyl-2,3'-bipyridin-5-yl)methyl]-2,5-dihydro -3H-pyrazolo[4,3-c]pyrido[3,2-e]pyridazin-3-one;

(±)-5-[(6'-Methyl-2,3'-bipyridin-5-yl)methyl]-2-(tetrahydro-2H-pyran-3-yl)-2,5-dihydro-3 H-pyrazolo[4,3-c]pyrido[3,2-e]pyridazin-3-one;

(±)-5-{[4-(1H-Pyrazol-1 -yl)phenyl]methyl}-2-(tetrahydro-2H-pyran-3-yl)-2,5 -dihydro-3H-pyrazolo[4,3-c]pyrido[3,2-e]pyridazin-3-one;

(±)-5-{[4-(6-Methylpyridin-3-yl)phenyl]methyl}-2-(tetrahydro-2H-pyran-3 -yl)-2,5 -dihydro -3H-pyrazolo[4,3-c]pyrido[3,2-e]pyridazin-3-one;

(±)-2-(Tetrahydro-2H-pyran-3 -yl)-5 -{[4-(1 ,3-thiazol-4-yl)phenyl]methyl}-2,5-dihydro-3H-pyrazolo[4,3-c]pyrido[3,2-e]pyridazin-3-one;

(±)-5-{[4-(6-Hydroxypyridin-3-yl)phenyl]methyl}-2-(tetrahydro-2H-pyran-3 -yl)-2,5 -dihydro -3H-pyrazolo [4,3-c]pyrido[3,2-e]pyridazin-3-one;

2-(2-Methylphenyl)-5 - {[4-(1H-pyrazol-1-yl)phenyl]methyl}-2,5 -dihydro-3H-pyrazolo [4,3-c]thieno[2,3-e]pyridazin-3-one;

(±)-5- {[4-(1H-Pyrazol-1-yl)phenyl]methyl}-2-(tetrahydro-2H-pyran-3 -yl)-2,5 -dihydro-3H-pyrazolo[4,3-c]thieno[2,3-e]pyridazin-3-one;

(±)-5- {[4-(6-Methylpyridin-3-yl)phenyl]methyl}-2-(tetrahydro-2H-pyran-3 -yl)-2,5 -dihydro -3H-pyrazolo[4,3-c]thieno[2,3-e]pyridazin-3-one;

(±)-5- {[4-(2-Methylpyridin-4-yl)phenyl]methyl}-2-(tetrahydro-2H-pyran-3 -yl)-2,5 -dihydro -3H-pyrazolo[4,3-c]thieno[2,3-e]pyridazin-3-one;

or a pharmaceutically acceptable salt thereof.

19. A pharmaceutical composition comprising a therapeutically effective amount of a compound of claim 1, or a pharmaceutically acceptable salt thereof, and a pharmaceutically acceptable carrier.

* * * * *